United States Patent
Stenqvist

(10) Patent No.: US 11,154,217 B2
(45) Date of Patent: *Oct. 26, 2021

(54) SYSTEM AND METHOD FOR DETERMINATION OF TRANSPULMONARY PRESSURE IN A PATIENT CONNECTED TO A BREATHING APPARATUS

(71) Applicant: The Lung Barometry Sweden AB, Viken (SE)

(72) Inventor: Ola Stenqvist, Viken (SE)

(73) Assignee: The Lung Barometry Sweden AB, Viken (SE)

( * ) Notice: Subject to any disclaimer, the term of this patent is extended or adjusted under 35 U.S.C. 154(b) by 799 days.

This patent is subject to a terminal disclaimer.

(21) Appl. No.: 15/583,308

(22) Filed: May 1, 2017

(65) Prior Publication Data

US 2017/0332943 A1 Nov. 23, 2017

Related U.S. Application Data

(63) Continuation of application No. 14/231,768, filed on Apr. 1, 2014, now Pat. No. 9,655,544, which is a
(Continued)

(30) Foreign Application Priority Data

Jun. 19, 2010 (EP) .................................. 10166587

(51) Int. Cl.
*A61M 16/00* (2006.01)
*A61B 5/08* (2006.01)
(Continued)

(52) U.S. Cl.
CPC ................ *A61B 5/085* (2013.01); *A61B 5/08* (2013.01); *A61B 5/0871* (2013.01); *A61B 5/091* (2013.01);
(Continued)

(58) Field of Classification Search
CPC .......... A61M 16/0003; A61M 16/0057; A61M 16/0069; A61M 16/026; A61M 16/06;
(Continued)

(56) References Cited

U.S. PATENT DOCUMENTS

| | | | |
|---|---|---|---|
| 4,214,593 | A | 7/1980 | Imbruce et al. |
| 8,497,379 | B2 | 7/2013 | Choi-Sledeski et al. |

(Continued)

FOREIGN PATENT DOCUMENTS

| | | | |
|---|---|---|---|
| CN | 1373670 A | 10/2002 | |
| CN | 1956679 A | 5/2007 | |

(Continued)

OTHER PUBLICATIONS

Talmor, Nov. 13, 2008, NEJM, 359; 20, 2095-2107.*
(Continued)

*Primary Examiner* — Bradley H Philips
(74) *Attorney, Agent, or Firm* — Knobbe, Martens, Olson & Bear, LLP

(57) ABSTRACT

A breathing apparatus (1) is disclosed that is adapted to determine a transpulmonary pressure in a patient (125) when connected to said breathing apparatus. A control unit (105) is operable to set a first mode of operation for ventilating said patient with a first Positive End Expiratory Pressure (PEEP) level; set a second mode of operation for ventilating said patient with a second PEEP level starting from said first PEEP level; and determine said transpulmonary pressure (Ptp) based on a change in end-expiratory lung volume (ΔEELV) and a difference between said first PEEP level and said second PEEP level (ΔPEEP). Furthermore, a method and computer program are disclosed.

25 Claims, 17 Drawing Sheets

Related U.S. Application Data continuation of application No. 13/704,836, filed as application No. PCT/EP2011/060264 on Jun. 20, 2011, now Pat. No. 8,701,663.

(60) Provisional application No. 61/469,100, filed on Mar. 30, 2011, provisional application No. 61/356,589, filed on Jun. 19, 2010.

(51) Int. Cl.
| | |
|---|---|
| *A61B 5/085* | (2006.01) |
| *A61B 5/091* | (2006.01) |
| *A61M 16/20* | (2006.01) |
| *A61B 5/087* | (2006.01) |
| *A61B 5/097* | (2006.01) |
| *A61B 5/00* | (2006.01) |
| *A61M 16/06* | (2006.01) |
| *A61M 16/12* | (2006.01) |

(52) U.S. Cl.
CPC ............ *A61B 5/097* (2013.01); *A61B 5/4836* (2013.01); *A61B 5/7225* (2013.01); *A61B 5/7278* (2013.01); *A61B 5/7282* (2013.01); *A61M 16/0003* (2014.02); *A61M 16/0057* (2013.01); *A61M 16/0069* (2014.02); *A61M 16/026* (2017.08); *A61M 16/06* (2013.01); *A61M 16/204* (2014.02); *A61M 16/205* (2014.02); *A61M 16/208* (2013.01); *A61M 16/12* (2013.01); *A61M 2016/0021* (2013.01); *A61M 2016/0027* (2013.01); *A61M 2016/0039* (2013.01); *A61M 2016/0042* (2013.01); *A61M 2205/3331* (2013.01); *A61M 2210/105* (2013.01); *A61M 2230/46* (2013.01)

(58) Field of Classification Search
CPC .. A61M 16/12; A61M 16/204; A61M 16/205; A61M 16/208; A61M 2016/0021; A61M 2016/0027; A61M 2016/0039; A61M 2016/0042; A61M 2205/3331; A61M 2210/105; A61M 2230/46
See application file for complete search history.

(56) References Cited

U.S. PATENT DOCUMENTS

| | | | |
|---|---|---|---|
| 8,701,663 B2* | 4/2014 | Stenqvist | A61B 5/08 128/204.21 |
| 9,655,544 B2* | 5/2017 | Stenqvist | A61B 5/08 |
| 2007/0049843 A1* | 3/2007 | Derchak | A61B 5/0806 600/538 |
| 2007/0062533 A1 | 3/2007 | Choncholas | |
| 2007/0179087 A1 | 8/2007 | Gelfand et al. | |
| 2009/0165797 A1* | 7/2009 | Cong | A61M 16/022 128/204.23 |
| 2010/0228142 A1* | 9/2010 | Sinderby | A61B 5/08 600/533 |
| 2012/0128759 A1 | 5/2012 | Lahn et al. | |
| 2012/0325209 A1 | 12/2012 | Quintin | |

FOREIGN PATENT DOCUMENTS

| | | |
|---|---|---|
| EP | 1295620 A1 | 3/2003 |
| WO | WO 2007082384 A1 | 7/2007 |
| WO | WO 2011/027243 A1 | 3/2011 |

OTHER PUBLICATIONS

Gattinoni et al., "Acute respiratory distress syndrome caused by pulmonary and extrapulmonary disease. Different syndromes?", Am J Respir Crit Care Med., vol. 158, No. 1, Jul. 1998 (Jul. 1, 1998), pp. 3-11.

Olegard et al., "Estimation of functional residual capacity at the bedside using standard monitoring equipment: a modified nitrogen washout/washin technique requiring a small change of the inspired oxygen fraction", Anesth Analg., vol. 101, No. 1, Jul. 2005 (Jul. 1, 2005), pp. 206-212.

Pelosi et al.: "Recruitment and derecruitment during acute respiratory failure: an experimental study", Am J Respir Crit Care Med., vol. 164, No. 1, Jul. 1, 2001 (Jul. 1, 2001), pp. 122-130.

Mols et al., "Volume-dependent compliance in ARDS: proposal of a new diagnostic concept.", Intensive Care Med., 1995, vol. 25, pp. 1084-1091,.

Talmore et al., "Mechanical ventilation guided by esophageal pressure in acute lung injury", N. Engl. J. Med., 2008, vol. 359 (20): 2095-2104.

International Search Report for PCT/EP2011/060264 dated Oct. 28, 2011.

Office Action in Japanese Application No. 2017-117320, dated May 22, 2019 and English Translation.

* cited by examiner

SYSTEM AND METHOD FOR DETERMINATION OF TRANSPULMONARY PRESSURE IN A PATIENT CONNECTED TO A BREATHING APPARATUS

CROSS-REFERENCE TO RELATED APPLICATIONS

This application is a continuation application of U.S. patent application Ser. No. 14/231,768, entitled "System and Method for Determination of Transpulmonary Pressure in a Patient Connected to a Breathing Apparatus," filed on Apr. 1, 2014, and published as U.S. Patent Application Publication No. 2014/0296730 on Oct. 2, 2014, which is a continuation application of U.S. patent application Ser. No. 13/704,836, entitled "System and Method for Determination of Transpulmonary Pressure in a Patient Connected to a Breathing Apparatus," filed on Mar. 29, 2013 and issued as U.S. Pat. No. 8,701,663 on Apr. 22, 2014, which is a U.S. National Phase application under 35 U.S.C. § 371 of International Application No. PCT/EP2011/060264, filed Jun. 20, 2011, designating the United States of America and published in the English language as WO2011/157855 on Dec. 12, 2011, which claims priority to U.S. Provisional Patent Application No. 61/356,589, and European Patent Application EP10166587.5, both filed Jun. 19, 2010, and U.S. Provisional Patent Application No. 61/469,100 filed Mar. 30, 2011, all entitled "A System and Method for Determination of Transpulmonary Pressure in a Patient Connected to a Breathing Apparatus", which are incorporated herein by reference in their entirety for all purposes.

BACKGROUND OF THE INVENTION

Patients with acute respiratory failure in need for ventilator treatment in intensive care units show highly varying pathophysiologic conditions of the respiratory system. With regard to the heterogeneity of acute lung injury (ALI) and the more severe acute respiratory distress syndrome (ARDS), the percentage of potentially recruitable lung, i.e. lung tissue that was collapsed but can be opened by a high pressure inflation is up to approximately 60%. One important reason for the heterogeneity is whether the patient has ARDS of pulmonary or extrapulmonary origin, i.e. whether it is the lungs per se or the chest wall and the diaphragm that are mainly affected. In most cases of respiratory failure, both the mechanical conditions of the lung, the stiffness (elastance=E) of the lungs (El) and the stiffness of the containing wall, (Ec), chest wall and diaphragm, play an important role.

During ventilator treatment the mechanical properties of the total respiratory system was hitherto determined by the combined effect of stiffness of the lungs and the stiffness of the chest wall/diaphragm working in series. The lung is a compliant unit within another compliant unit, namely the chest wall and the diaphragm. For optimal ventilator treatment, where risks and benefits of the treatment are balanced, knowledge of the stiffness of the chest wall in relation to the stiffness of the lung is of outmost importance.

For instance, the risk of inducing damage to the sensitive lung tissue by the ventilator treatment is increasing when the lung is very stiff and the chest wall/diaphragm is very soft, where most of the airway pressure generated by the ventilator during inspiration acts solely on the lung, i.e. a high transpulmonary pressure is present. Very little of the pressure applied by the ventilator to the patient is transmitted to the surrounding chest wall and diaphragm.

On the other hand, in a case where the stiffness of the chest wall and especially the diaphragm is increased, e.g. by abdominal inflammation, with resulting high sub-diaphragmatic pressures, the lung will be limited in its expansion by the stiffness of the chest wall and diaphragm, and the transpulmonary pressure will be low. The risk of ventilator induced lung injury will be reduced. This was shown by Talmor et al, in a randomised study on oesophageal pressure guided mechanical ventilation in ARDS patients (Talmor et al NEJM 2008; 359(20): 2095-2104).

As measurement of the transpulmonary pressure is difficult, a measurement of the oesophageal pressure is used as a surrogate of pleural pressure instead of measuring pleural pressure directly. The oesophageal pressure is used as an indirect measure of how much airway pressure is transferred through the lung to the chest wall and diaphragm during assisted controlled ventilation. This makes it possible to give an estimate of the stiffness of the chest wall/diaphragm based on the oesophageal pressure.

The combined stiffness of the lungs and chest wall/diaphragm, total respiratory system stiffness (Etot), is the sum of the lung stiffness and the chest wall/diaphragm stiffness. The stiffness of the lung may thus indirectly determined by subtraction of Ec from Etot. The calculation of chest wall and lung compliance is based on the tidal difference in end-expiratory and end inspiratory oesophageal and airway pressures ($\Delta$Poes, $\Delta$Paw).

However, there are practical difficulties of performing the oesophageal pressure measurement. Oesophageal pressure is measured by means of catheter like elongate pressure monitoring devices, such as disclosed in U.S. Pat. No. 4,214,593. The device comprises a nasogastric tube provided with an oesophageal balloon cuff.

The correct placement of the oesophageal balloon catheter in the oesophagus, especially in patients who already have a stomach tube inserted through the oesophagus, has shown to be very difficult. It can be compared with forwarding a soft spaghetti through a branched tubing structure without vision during this action.

Moreover, the performance of the oesophageal balloon as a transmitter of oesophageal pressure is influenced by how much it is preinflated and how much mediastinal weight, i.e. weight of the heart is superimposed on the balloon. Also, the reliability of the measurements has been questioned as oesophageal pressure is a substitute measure of pleural pressures, which are different in different places, due to gravitational forces and its proximity to the diaphragm, where abdominal pressure and diaphragmatic stiffness have a greater impact.

In addition, an oesophagal balloon measurement provides a pressure measurement only for the horizontal plane in which the measurement is done. Depending on the positioning in the patient thus different measurement values will be obtained e.g. due to gravitational forces acting on the patient body and in particular the lung, directly or indirectly via the weight if other organs in the thorax of the patient. There is a need of providing a measure representative of all transpulmonary pressures irrespective of the position thereof, avoiding the influence of factors such as gravitational forces acting on the patient body.

Thus, besides the costs for the catheters and their use, the practical positioning difficulties and doubtful reliability of measurement values obtained have resulted in a very limited clinical use of such oesophageal balloon catheter.

Another important issue is that measuring pleural pressure directly in the pleural cavity surrounding the lungs is practically not possible as the pleural space usually is very small and a risk of puncturing the lungs is impending but should be avoided by any means. It is highly hazardous to measure the pleural pressure due to the risk of puncturing the lung. Therefore, it has been attempted to use oesophagal pressure as a surrogate as described above.

Hence, there is a need for a new or alternative way of measuring or determining transpulmonary pressure in a patient connected to a breathing apparatus.

European Patent publication EP1295620 discloses a breathing apparatus for use in the examination of pulmonary mechanics of a respiratory system.

TALMOR DANIEL ET AL: "Mechanical Ventilation Guided by Esophageal Pressure in Acute Lung Injury", NEW ENGLAND JOURNAL OF MEDICINE vol. 359, no. 20, November 2008 (2008-11), pages 2095-2104, discloses a study concerning randomly assigned patients with acute lung injury or ARDS to undergo mechanical ventilation with PEEP adjusted according to measurements of esophageal pressure (the esophageal-pressure-guided group) or according to the Acute Respiratory Distress Syndrome Network standard-of-care recommendations.

International PCT publication 2007/082384 discloses a method for determining dynamically respiratory feature in spontaneously breathing patients receiving mechanical ventilatory assist.

An object of the present invention may be regarded as direct determination of transpulmonary pressure without the use of oesophageal pressure measurements.

An improved or alternative system, computer program and/or method for determination of transpulmonary pressure without the use of indirect measures, such as oesophageal pressure measurements would be advantageous. Moreover, it would be advantageous and to provide such a system, computer program and/or method allowing for increased flexibility when using existing breathing apparatuses, cost-effectiveness by avoiding purchase and use of additional equipment needed for the transpulmonary pressure determination, and user friendliness thereof would be advantageous. It would also be advantageous if such a measurement or determination provided a mean value for the transpulmonary pressure, i.e. a measure representative of all transpulmonary pressures irrespective of the position thereof, e.g. due to gravitational forces acting on the patient body.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a breathing apparatus, computer program, and method according to the appended patent claims.

According to an aspect of the invention, a breathing apparatus is provided having an inspiratory pressure sensor and flow sensor, an expiratory pressure sensor and flow sensor, inspiratory valve, an expiratory valve, and a control unit that is adapted to determine a transpulmonary pressure in a patient when connected to the breathing apparatus. The control unit is operable to a) set the breathing apparatus in a first mode of operation for ventilating the patient with a first Positive End Expiratory Pressure (PEEP) level; b) set the breathing apparatus in a second mode of operation for ventilating the patient with a second PEEP level starting from the first PEEP level, wherein the second PEEP level is based on a target PEEP level different from the first PEEP level; c) determine a change in end-expiratory lung volume ($\Delta$EELV) from a difference of end-expiratory lung volume (EELV) present at the first PEEP level and the second PEEP level; and determine the transpulmonary pressure (Ptp) based on the change in end-expiratory lung volume ($\Delta$EELV) and a difference between the first PEEP level and the second PEEP level ($\Delta$PEEP).

According to a further aspect of the invention, a computer-readable medium is provided having embodied thereon a computer program for processing by a computer. The computer program comprises a plurality of code segments for determining a transpulmonary pressure (Ptp) in a patient connected to a breathing apparatus. The code segments comprise a first code segment for establishing a first Positive End Expiratory Pressure (PEEP) level; a second code segment for changing a target PEEP level from the first PEEP level to a second PEEP level, different from the first PEEP level, and a third code segment for establishing the second PEEP level starting from the first PEEP level; a fourth code segment for determining a change in end-expiratory lung volume ($\Delta$EELV) from a difference of end-expiratory lung volume (EELV) present at the first PEEP level and the second PEEP level; and a fifth code segment for determining the transpulmonary pressure (Ptp) based on the change in end-expiratory lung volume ($\Delta$EELV) and a difference between the first PEEP level and the second PEEP level ($\Delta$PEEP).

According to another aspect of the invention, a method of internally in a breathing apparatus is provided for determining a transpulmonary pressure (Ptp) in a patient connected to a breathing apparatus. The method comprises establishing a first Positive End Expiratory Pressure (PEEP) level; changing a target PEEP level from the first PEEP level to a second PEEP level, different from the first PEEP level, and establishing the second PEEP level starting from the first PEEP level; determining a change in end-expiratory lung volume ($\Delta$EELV) from a difference of end-expiratory lung volume (EELV) present at the first PEEP level and the second PEEP level; and determining the transpulmonary pressure (Ptp) based on the change in end-expiratory lung volume ($\Delta$EELV) and a difference between the first PEEP level and the second PEEP level ($\Delta$PEEP).

The above computer program is preferably provided for enabling carrying out of the above method.

Further embodiments of the invention are defined in the dependent claims, wherein features for the second and subsequent aspects of the invention are as for the first aspect mutatis mutandis.

Embodiments of the invention avoid the use of indirect measurements of transpulmonary pressure, such as based on oesophagal pressure measurements.

Embodiments of the invention also provide for a user friendly way of determining transpulmonary pressure.

Embodiments of the invention may be implemented with existing breathing apparatuses without adding additional sensor units to the apparatus.

Embodiments of the invention provide for a measure of the transpulmonary pressure without measuring the pleural pressure.

Embodiments of the invention provide for patient safe and non-hazardous way of determining the transpulmonary pressure.

Embodiments of the invention provide for automated determination of transpulmonary pressure.

Embodiments of the invention provide for deflection points at non-linear compliances. A lower inflection point and/or an upper deflection point may be determined.

In embodiments the transpulmonary pressure is determined during assisted and/or controlled ventilation of a patient. The patient is not spontaneously breathing.

Some embodiments provide for determination of the transpulmonary pressure in a system and method when the patient is connected to the breathing apparatus non-invasively, e.g. via breathing tubing and a face mask. Leakage should be kept at a minimum or can be detected and suitably compensated in volume and pressure measurements in ways known to use by the skilled person when reading the present description.

Transpulmonary pressure determined by such embodiments may be used to adapt a ventilation strategy of the patient. Adaptation of ventilation strategy may be made in an automated way, upon user selection and based on the determined transpulmonary pressure. Thus, lung injury of the patient may be effectively avoided.

The transpulmonary pressure (Ptp) can be defined as the pressure that keeps the lung, when inflated in a distended condition, stretched against the inner of the chest wall and the diaphragm. The transpulmonary pressure (Ptp) is the difference between the pressure in the trachea, also called lung pressure (Pl), and the pleural pressure in the pleura, located inside the chest wall and outside of the lung, (Pcw).

Transpulmonary pressure determined by embodiments is a mean value for the transpulmonary pressure, denoted Ptp hereinafter is thus Ptp(mean). This is an advantageous measure representative of all transpulmonary pressures irrespective of the position thereof in relation to the lung.

In summary, $\Delta$EELV/$\Delta$PEEP provides a calculation value for CL. This is provided for the pressure/volume range in which a PEEP step is performed. A most advantageous measurement is based on spirometric determination of the ingoing calculation parameters. At small PEEP steps and volumes, the value is at an optimum. Small PEEP steps are in this context up to 3 cmH$_2$O $\Delta$PEEP. A clinically preferable range is 2-3 cmH$_2$O. Small volumes include $\Delta$EELV being in the range of total tidal volume at 0 PEEP. In absolute measures this is for instance 6 ml/kg predicted body weight for adult patients, which is about 400 ml for a 70 kg adult. This provides for the most accurate determination of $P_{TP}$ while providing a lung protective strategy.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
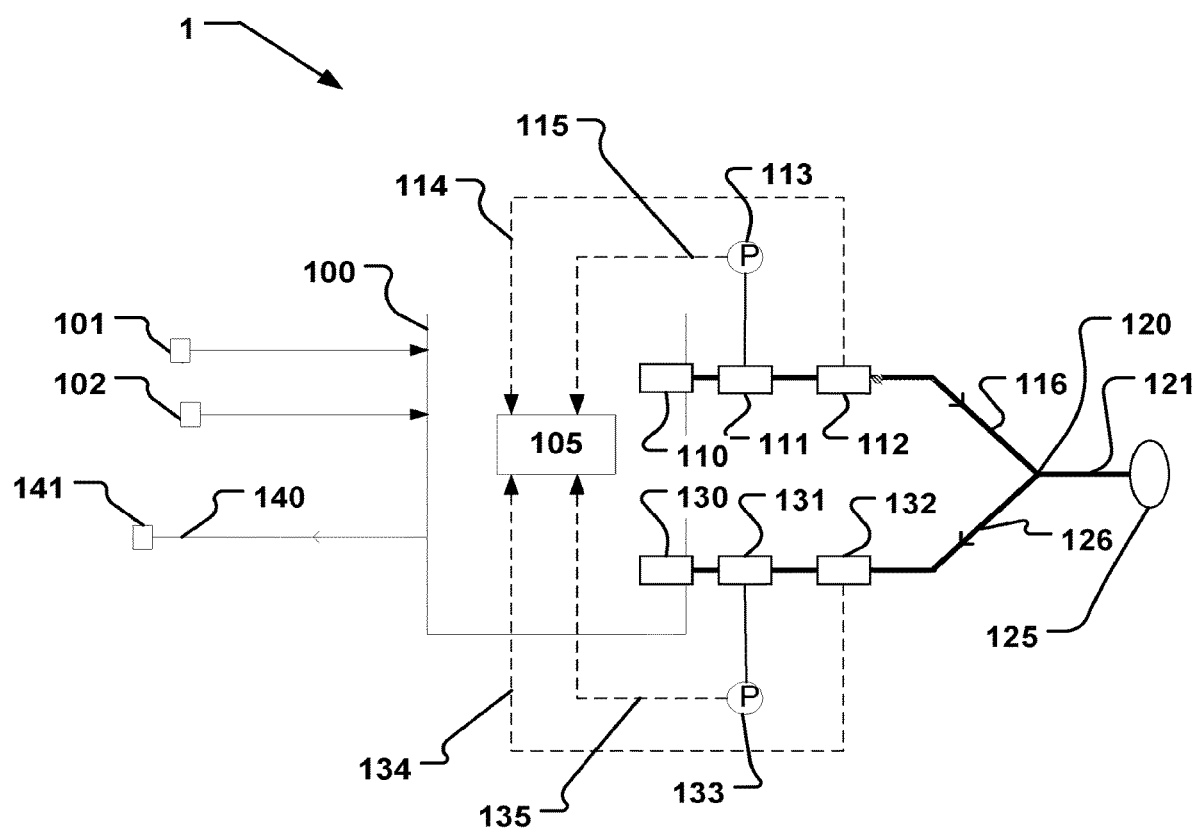
FIG. 1 is a schematic illustration of an embodiment of a breathing apparatus.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description describes an embodiment applicable to a breathing apparatus and in particular to a respiratory ventilator in use connected to sources of pressurized gas. However, it will be appreciated that the invention is not limited to this application but may be applied to many other breathing apparatuses, including for example fan driven breathing apparatuses. The embodiment described is a breathing apparatus in form of an intensive care respiratory ventilator. However, other embodiments may comprise anaesthetic vaporizers, breathing circles, etc. connected to the breathing apparatus without deviating from the invention. The invention is suited for all groups of patients, including adult/paediatric patients or neonatal patients.

FIG. 1 is a schematic illustration of an embodiment of a breathing apparatus 1. In the embodiment a first source of pressurized gas 101, such as for air, and optionally further sources of pressurized gas 102, such as for oxygen and/or nitrous oxide, are arranged for providing input gas to the breathing apparatus 1, usually to a housing 100. A suitable mixture of gas is by means of one or more inspiratory gas valves 110 controllably delivered to a patient 125 via an inspiratory branch 116.

The inspiratory branch 116 comprises suitable tubing for conveying the gas mixture via a Y-piece 120 and a patient connection 121, such as a face mask, laryngeal mask, a tracheal cannula, or an endotracheal tube, to the patient 125 during an inspiratory phase. Inspiratory pressure is measured by means of a pressure transducer 113, e.g. at an inspiratory sampling point 111. Inspiratory flow towards the patient is measured by means of an inspiratory flow transducer 112.

An expiratory branch 126 comprises suitable tubing for conveying the gas from the Y-piece 120. The gas in the expiratory branch may comprise exhaled gas from the patient 125 during an expiratory phase, and/or a bias flow from the inspiratory branch 116 passing the Y-piece 120 directly without entering the patient 125. An expiratory valve 130 controls the gas flow in the expiratory branch. During inspiration it is usually closed. Expiratory pressure is measured by means of a pressure transducer 131, e.g. at an expiratory sampling point 131. Expiratory flow to the expiratory valve 130 is measured by means of an expiratory flow transducer 132. Gas passing the expiratory valve 140 is conveyed further to the surrounding environment or an evacuation system 141 via an exhaust 140.

A control unit 105 provides for inspiratory breathing patterns to the patient 125 during the inspiratory phase and expiratory control of release of patient gas from the patient during the expiratory phase. The control unit is provided with signals from the inspiratory and expiratory pressure and flow meters via lines 114, 115, 134, and 135, respectively.

The control unit 105 is adapted to determine a transpulmonary pressure Ptp in a patient 125 connected to the breathing apparatus 1. The control unit 105 is adapted to control the breathing apparatus suitably by controlling the inspiratory valve 110 and the expiratory valve 130. Feedback and measurements of inspiratory flow and pressure, as well as expiratory flow and pressure are provided by the pressure transducers 113, 133 and flow transducers 112, 132, respectively. Measurement values are collected and stored in a memory circuit (not shown) for access by the control unit 105. Ptp is then calculated as described in more detail below. The obtained Ptp value may be used for adapting a continued ventilation strategy of the patient 125.

Thus controlled, the breathing apparatus 1 establishes an initial, first Positive End Expiratory Pressure (PEEP) level. The first PEEP level may be at ambient pressure, i.e. "0" relative to ambient pressure, or a positive pressure above ambient pressure. This first PEEP pressure is the starting PEEP pressure for the manoeuvre now initiated to provide measurement values for determining the Ptp.

A target PEEP level is changed from the first PEEP level to a second PEEP level, which is different from the first PEEP level. Based on this target PEEP level, subsequent inspiratory and expiratory phases are adjusted to establish the second PEEP level starting from the first PEEP level. This transition is elucidated in more detail below with reference to FIGS. 4, 5A-5F, and FIG. 6.

A change in end-expiratory lung volume ΔEELV is determined from a difference of end-expiratory lung volume (EELV) present at the first PEEP level and the second PEEP level.

The transpulmonary pressure Ptp is determined based on the change in end-expiratory lung volume ΔEELV and a difference between the first PEEP level and the second PEEP level, ΔPEEP. At every PEEP level, an end-expiratory pressure equilibrium is present, which means that ΔPEEP is equal to ΔPtp, which implies that $C_L$ is ΔEELV divided by ΔPEEP. This determination is elucidated in more detail below.

Hence, Ptp is determined without the need for and oesophageal pressure measurement, or another sensor to be inserted into the patient thorax for indirect measurement thereof. Ptp is determined solely from transducers commonly present in a breathing apparatus. Measurement values thereof at determined stages of the aforementioned PEEP level change manoeuvre are processed and the value for Ptp is provided for further processing.

Alternatively to an integrated control unit 105 for both controlling the ventilatory modes of the breathing apparatus 1 and the transpulmonary pressure determination, several control units may be provided, each having a dedicated specific task, and which are suitably operatively connected.

Figure 2:
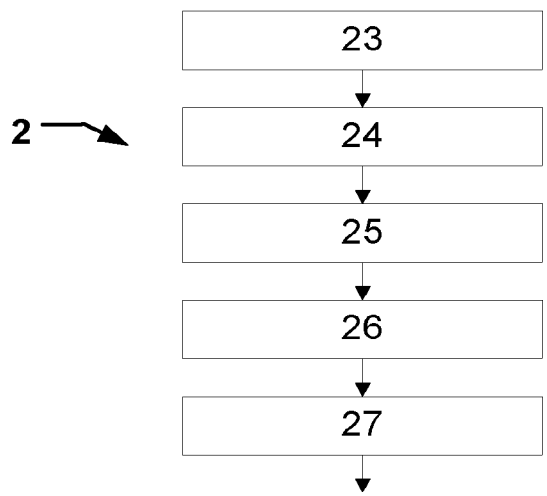
FIG. 2 is a flow chart of an embodiment of a method.

A further example for application of the invention is illustrated in FIG. 2 in a flow chart of a method 2. The method 2 is a method of determining a transpulmonary pressure Ptp in a patient connected to a breathing apparatus. The method comprises a number of steps. Initially, a first Positive End Expiratory Pressure (PEEP) level is determined as an existing PEEP level, or it is established in a step 23 to a desired first PEEP level. The target PEEP level is then changed in a step 24 from the first PEEP level to a second PEEP level, which is different from the first PEEP level. Based on this target PEEP level, the second PEEP level is established in a step 25 starting from the first PEEP level.

A change in end-expiratory lung volume ΔEELV is calculated in step 26 from a difference of end-expiratory lung volume EELV present at the first PEEP level and the second PEEP level. The transpulmonary pressure ΔPtp is then calculated in step 27 based on the change in end-expiratory lung volume ΔEELV and a difference between the first PEEP level and the second PEEP level ΔPEEP.

Figure 3:
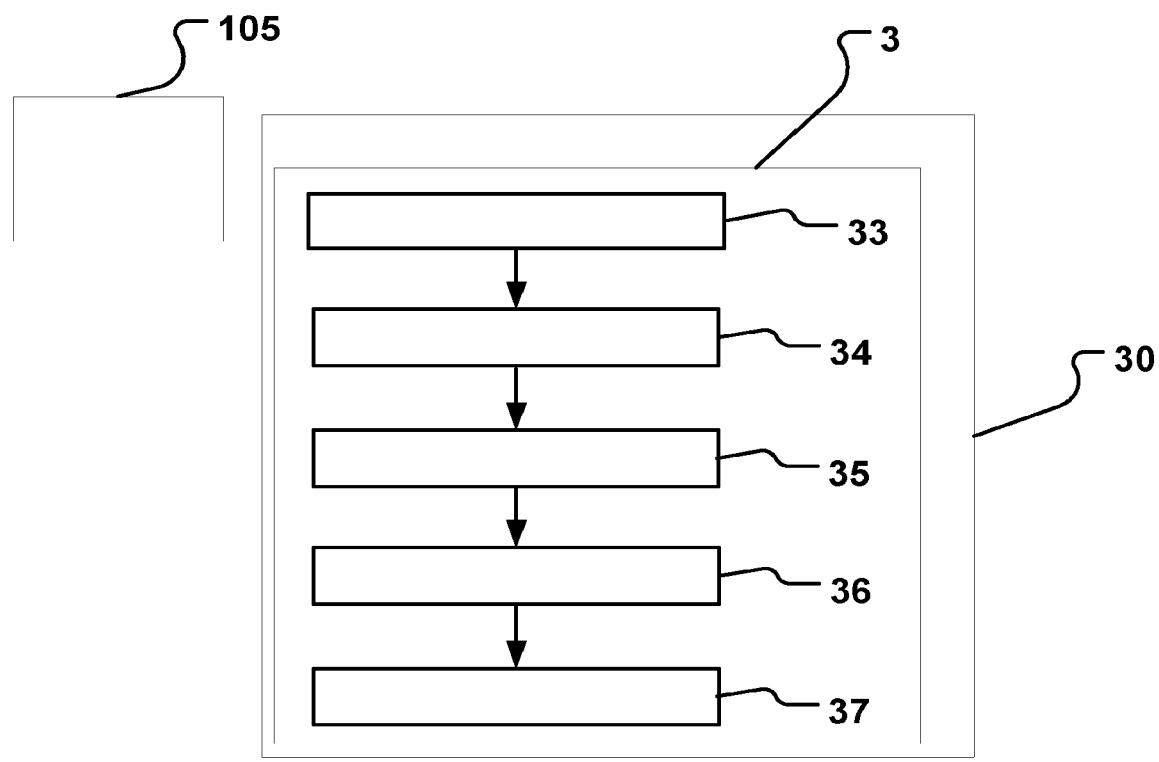
FIG. 3 is a schematic illustration of an embodiment of a computer program.

In another embodiment of the invention according to FIG. 3 a computer program 3 is illustrated stored on a computer readable medium 30 for executing by a processing device, such as the control unit 105. The computer program comprises a plurality of code segments for determining a transpulmonary pressure (Ptp) in a patient connected to a breathing apparatus. The code segments comprise a first code segment 33 for establishing a first Positive End Expiratory Pressure (PEEP) level; a second code segment 34 for changing a target PEEP level from the first PEEP level to a second PEEP level, different from the first PEEP level, and a third code segment 35 for establishing the second PEEP level starting from the first PEEP level; a fourth code segment 36 for determining a change in end-expiratory lung volume (ΔEELV) from a difference of end-expiratory lung volume (EELV) present at the first PEEP level and the second PEEP level; and a fifth code segment 37 for determining the transpulmonary pressure (Ptp) based on the change in end-expiratory lung volume (ΔEELV) and a difference between the first PEEP level and the second PEEP level (ΔPEEP).

The afore mentioned PEEP transition manoeuvre is now described in more detail. The manoeuvre is described as a method. It is understood that the method may be implemented by the afore described breathing apparatus 1 and the control unit 105 thereof, and/or a computer program.

A method of direct measurement of transpulmonary pressure is now described based on the assumption that the magnitude of the end-expiratory volume change following an end-expiratory pressure (PEEP) change is determined by the magnitude of the PEEP change and the compliance of the lung, i.e. the transpulmonary pressure Ptp change during a PEEP change equals the PEEP change.

A stepwise change in end-expiratory pressure (ΔPEEP) level results in a change in end-expiratory lung volume ΔEELV.

In this context the preferential method is to use a spirometric determination of the ΔEELV by measuring the cumulative difference in inspiratory and expiratory tidal volumes between the first and the second PEEP level, i.e. from a first PEEP level of equal inspiratory and expiratory volume until a second PEEP level equilibrium of inspiratory and expiratory tidal volumes are reached. This is implemented by using measurement signals from the inspiratory flow transducer 112 and the expiratory flow transducer of the breathing apparatus 1.

Figure 4:
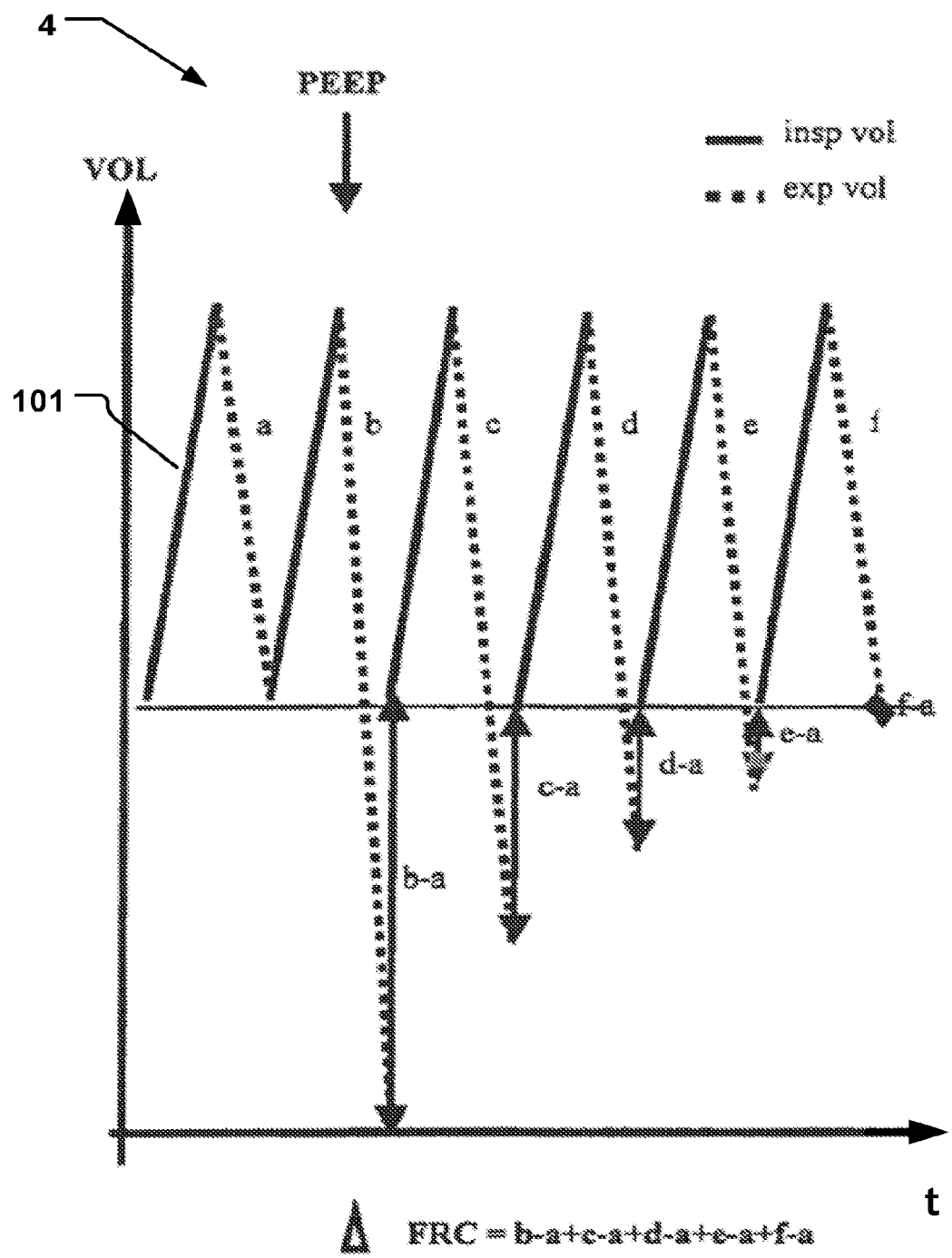
FIG. 4 is a graph illustrating a change in PEEP and resulting volume changes over time.

FIG. 4 is a graph 4 illustrating an example of such a change in PEEP and resulting volume changes over time. In the illustrated example, the second PEEP level is lower than the first PEEP level. The schematic graph 4 shows inspiratory (continuous line) and expiratory (dotted line) tidal volume measurements 101 over time t before. Curve segments a-f are reference signs for expiratory flow segments of expiratory phases of subsequent breathing cycles. An expiratory phase a is shown prior to the PEEP change. Expiratory phases after a release of PEEP (marked at the PEEP arrow in the figure) are shown at curve segments b, c, d, e and f during assisted and/or controlled mechanical ventilation of the breathing apparatus 1, here volume controlled ventilation.

The sum of the increase in expiratory volume (b–a+c–a+d–a+e–a+f–a) after the PEEP release until expiratory volume is stabilised at a new equilibrium is substantially the same as the expiratory volume before the PEEP release at (a). This sum is equal to the difference in end-expiratory lung volume EELV between the two PEEP levels.

An increase in EELV when increasing the PEEP from a first level to a second, higher level, is calculated correspondingly.

Alternatively, or in addition, $\Delta EELV$ can be determined by a number of other methods, such as CT scan before and after the PEEP change, FRC/EELV measurement by inert gas dilution technique before and after the PEEP change or by respiratory inductive plethysmography (RIP) or electric impedance tomography (EIT), or any other suitable method.

The end-expiratory volume increase after the first breath after the PEEP change is $$\Delta PEEP \times C_{TOT} = \Delta V1$$

wherein $C_{TOT}$ is the total compliance of the lung $C_L$ and chestwall/diaphragma $C_{CW}$, and the corresponding new end-expiratory transpulmonary pressure is $$\Delta PEEP \times C_{TOT}/CL = \Delta P1$$

The end-expiratory volume increase after the second breath after the PEEP change is $$(\Delta PEEP - \Delta P1) \times C_{TOT} = \Delta V2$$

and the corresponding end-expiratory mean transpulmonary pressure increase from $\Delta P1$ is $$\Delta V2/CL = \Delta P2$$

During the following breaths, the change in lung volume and the change in end-expiratory pressure will follow in the same way and the breath-by-breath volume and pressure changes will asymptotically decrease until the end-expiratory transpulmonary pressure has increased with the $\Delta PEEP$.

An example of increasing the second level of PEEP is now discussed, with reference to FIG. 5A-5F, which are pressure/volume graphs illustrating various stages of the course of lung filling following a step increase in PEEP.

In the example, the patient has a $C_{TOT}$ of 40, $C_{CW}$ of 95 and $C_L$ of 67 ml/cmH$_2$O. The total respiratory system course is illustrated by line 50 at $C_{TOT}$ in FIG. 5, the chest wall course is illustrated by line 51 at $C_{CW}$ in FIG. 5, and the lung course is illustrated by line 52 at $C_L$ in FIG. 5.

Figure 5A:
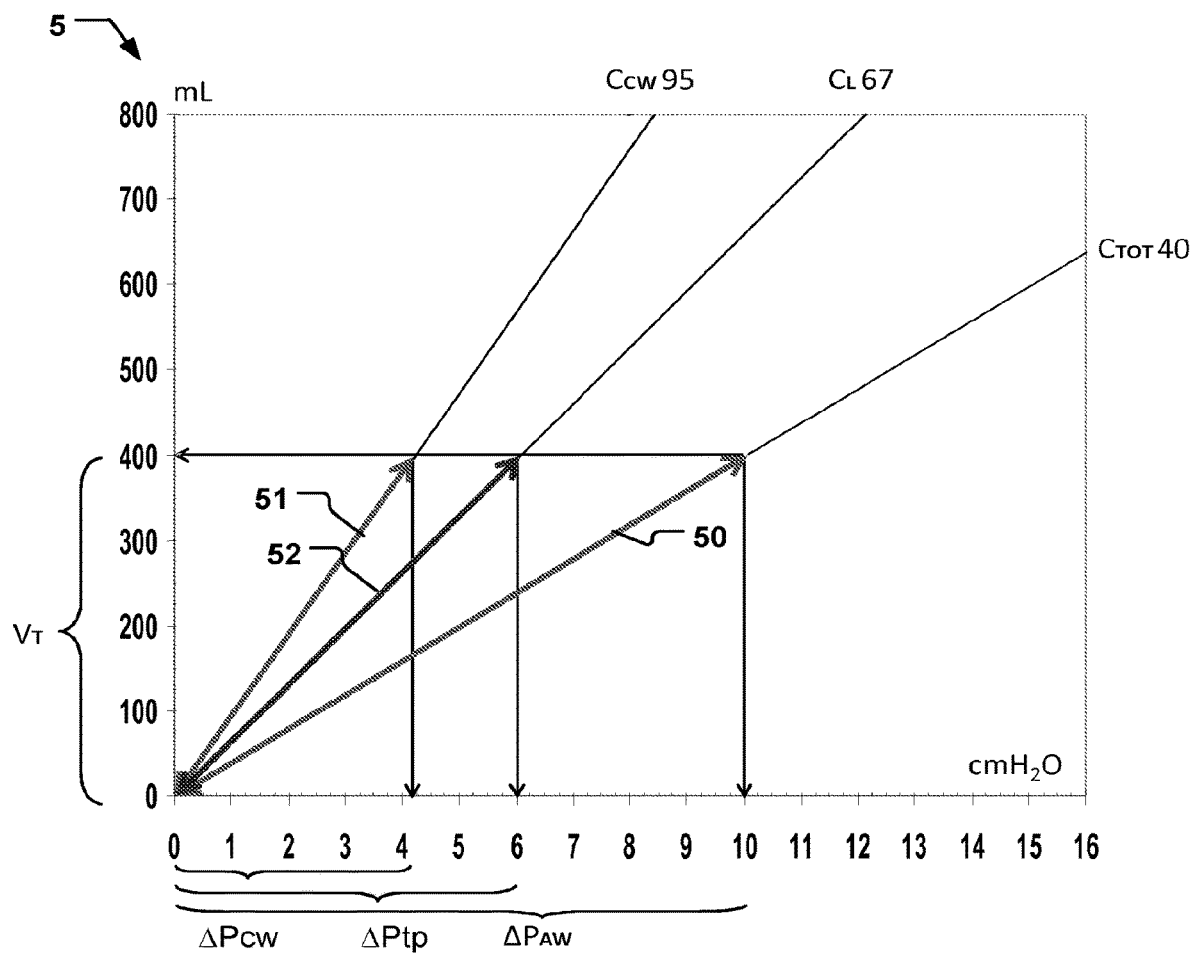
FIGS. 5A to 5F are pressure/volume graphs illustrating various stages of an embodiment of a method performed on a breathing apparatus.

FIG. 5A: ventilation is shown with a tidal volume of 400 ml and an airway pressure of 10 cmH$_2$O and an end-expiratory (PEEP) pressure of 0 cmH$_2$O. The tidal chest wall pressure variations ($\Delta Pcw$) is just above 4 cmH$_2$O resulting in a tidal transpulmonary pressure difference ($\Delta Ptp$) just below 6 cmH$_2$O.

Figure 5B:
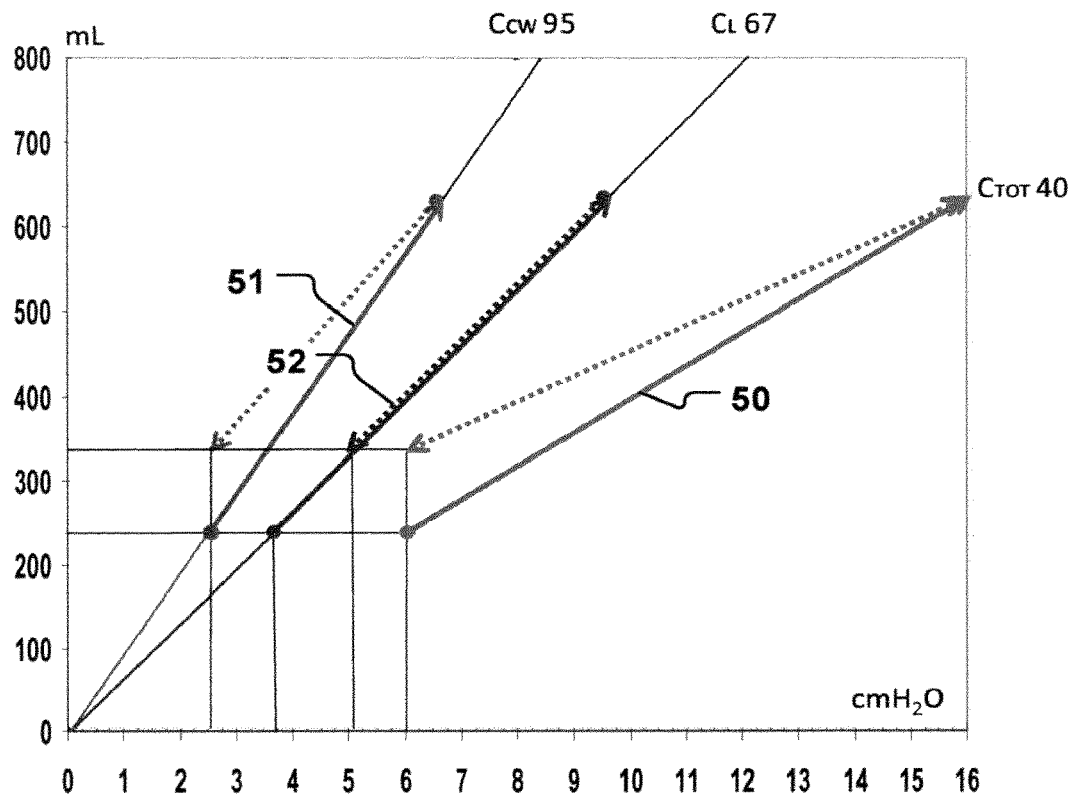

FIG. 5B: The first inspiration after changing the PEEP level to from the first PEEP level of 0 cmH$_2$O to the second PEEP level of 6 cmH$_2$O in the ventilator, inflates the lung with 6×40=240 ml ($\Delta PEEP \times C_{TOT}$) and increases the lung pressure with 3.6 cmH$_2$O as the change in lung pressure is the change in lung volume divided by the lung compliance, 240/67=3.6. Transpulmonary pressure increases at the same level as the lung pressure.

Figure 5C:
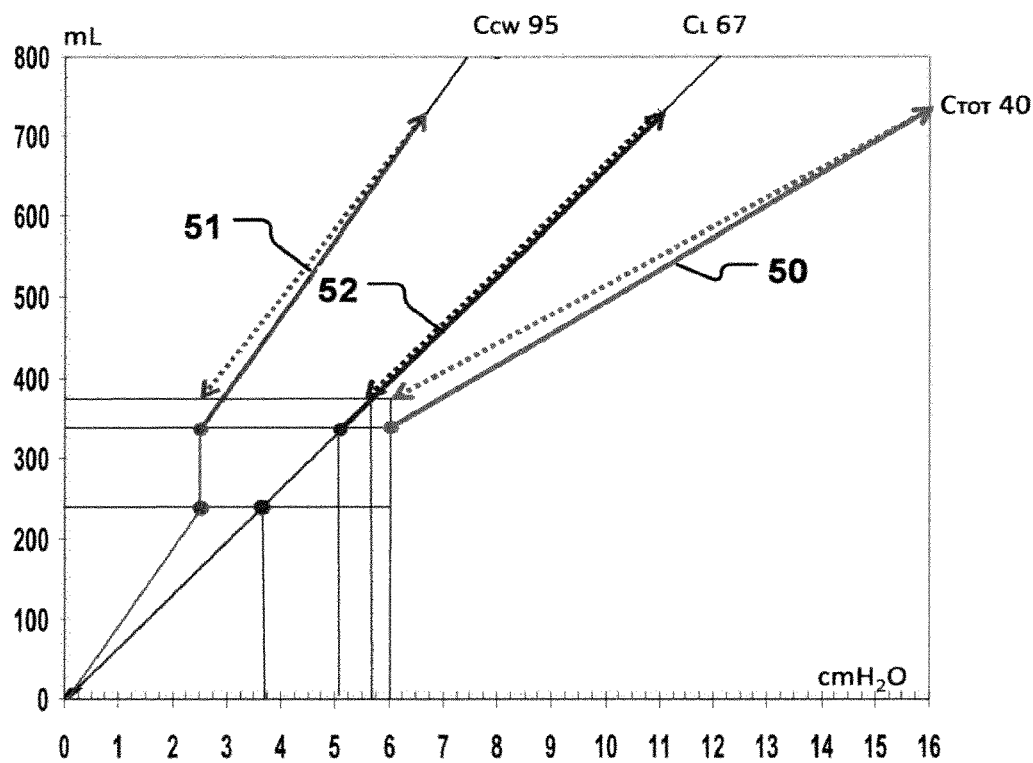

FIG. 5C: The second inspiration inflates the lung with (6–3.6)×40=96 ml (remaining transpulmonary pressure to the next PEEP level equilibrium). The transpulmonary pressure will increase with 96/67=1.4 cmH$_2$O.

Figure 5D:
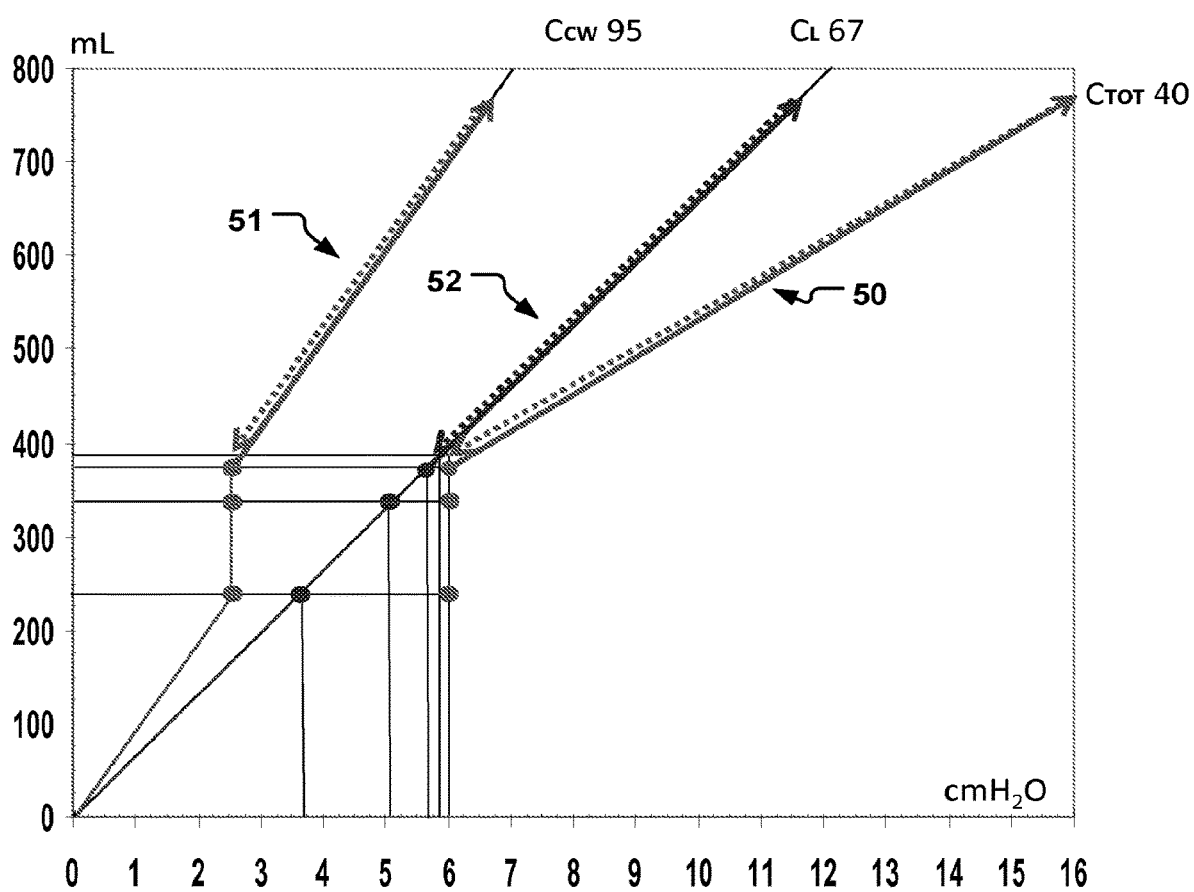

FIG. 5D: The following breaths will continue to expand the lung until a new equilibrium is reached, i.e., until as much volume has been added to the lung as determined by the compliance of the lung (67 ml/cmH$_2$O) and magnitude of the PEEP increase (6 cmH$_2$O), in this case 400 ml.

Figure 5E:
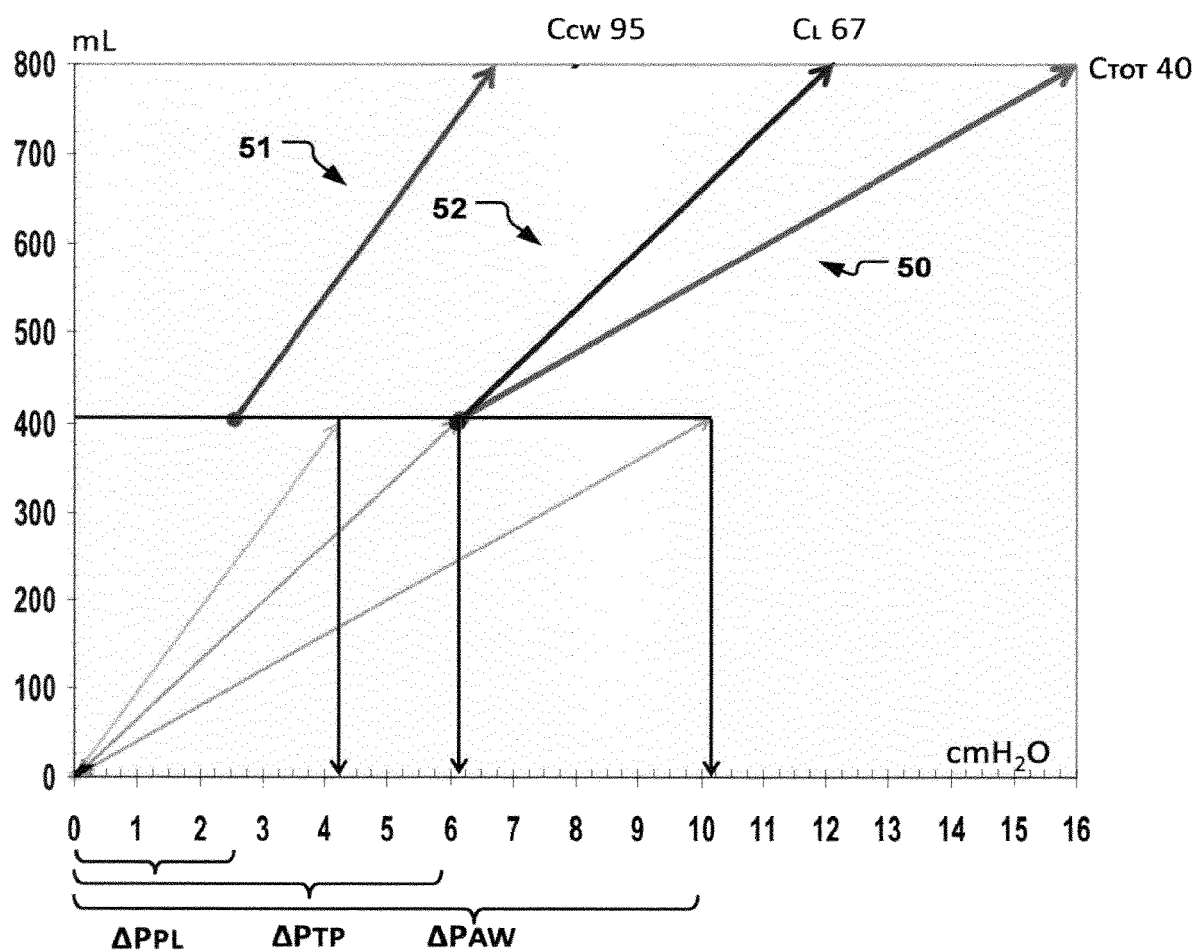

FIG. 5E: The first breath is shown after the volume/pressure equilibrium is reached at the new PEEP level of 6 cmH$_2$O. The total transpulmonary difference at that PEEP level is the $\Delta Ptp + PEEP$ over atmospheric pressure.

Figure 5F:
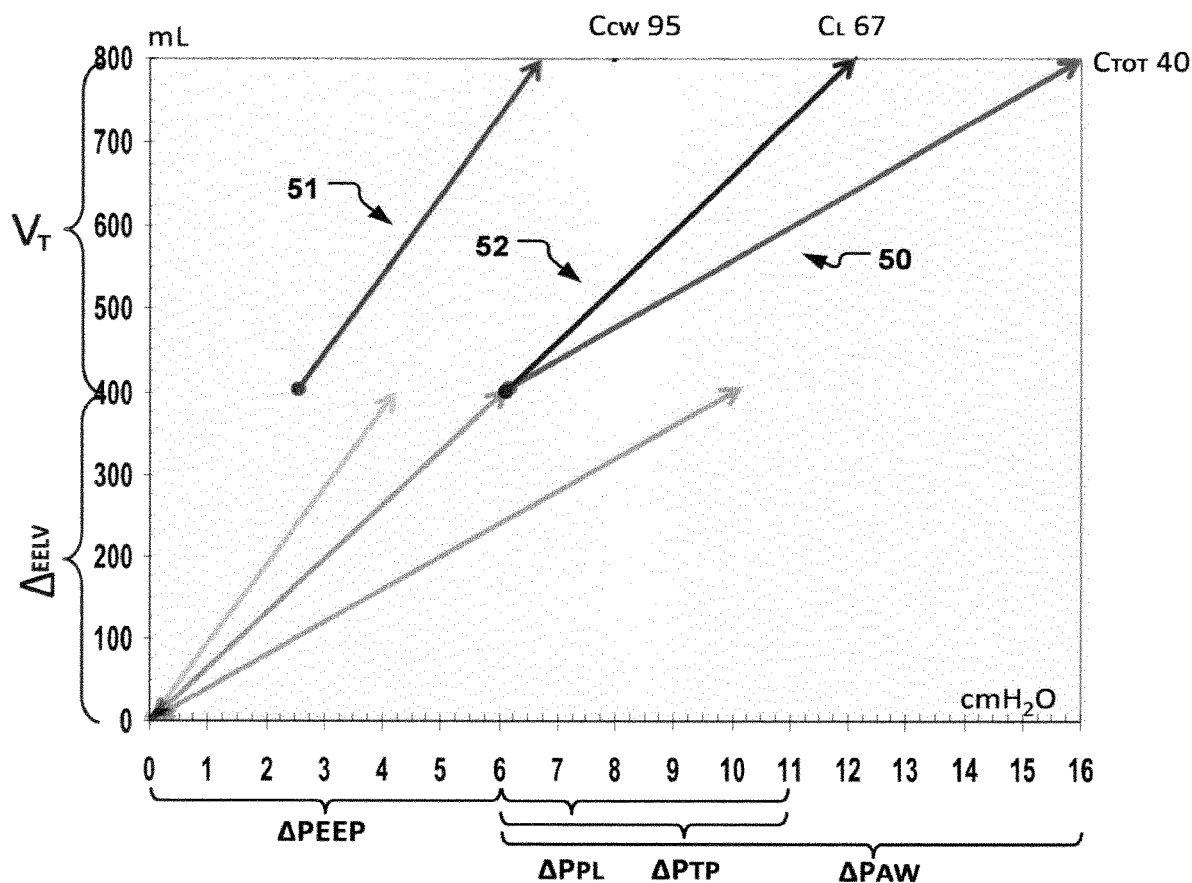

FIG. 5F: The tidal ventilation at new lung volume level is presented, showing that the ratio between the difference in lung volume between the second and first lung volume and the difference in end-expiratory pressure between the second and first PEEP levels are $\Delta EELV/\Delta PEEP$ which corresponds to the lung compliance, $C_L$.

The lung compliance $C_L$ is thus determined as $\Delta EELV/\Delta PEEP$.

The total respiratory system driving pressure ($\Delta Paw$) during mechanical ventilation is the difference between the airway pressure Paw during an end-inspiratory pause and an end-expiratory pause $$Paw - PEEP = \Delta Paw \quad (1)$$

The transpulmonary pressure difference ($\Delta Ptp$) between end of inspiration and end of expiration is the difference between the total respiratory system driving pressure ($\Delta Paw$) and the chest wall pressure difference ($\Delta Pcw$) between end of inspiration and end of expiration.

$$\Delta Ptp = \Delta Paw - \Delta Pcw \quad (2)$$

Total respiratory system compliance ($C_{TOT}$) is the ratio of the tidal volume $V_T$ to the total respiratory system driving pressure, namely the above airway pressure difference $\Delta Paw$:

$$C_{TOT} = V_T/\Delta Paw \quad (3)$$

The chest wall compliance ($Cc_W$) is the ratio of the tidal volume $V_T$ to the plural/chest wall pressure difference $\Delta Pcw$:

$$C_{CW} = V_T/\Delta Pcw \quad (4)$$

The lung compliance ($C_L$) is the ratio of the tidal volume $V_T$ to the transpulmonary pressure difference $$C_L = V_T/\Delta Ptp \quad (5)$$

Stiffness, elastance (E) is the reciprocal of compliance and $$E_{TOT} = 1/C_{TOT} \quad (6)$$

$$E_{CW} = 1/C_{CW} \quad (7)$$

$$E_L = 1/C_L \quad (8)$$

The lung elastance is the difference between the total respiratory system elastance and the chest wall elastance $$E_L = E_{TOT} - E_{CW} \quad (9)$$

During tidal breathing, at a stable PEEP level, the lung elastance or compliance cannot be determined without measuring the oesophageal pressure and then only indirectly calculated as the difference between total respiratory system stiffness and chest wall/diaphragmatic stiffness.

The Transpulmonary Pressure

A $C_{TOT}$ at the first PEEP level, which is equal to the $C_{TOT}$ of the second PEEP level indicates that lung compliance is linear over the existing pressure range and the transpulmonary pressure can be calculated as $$\Delta P_{TP} = \Delta Paw \times E_L / E_{TOT} \quad (10)$$

Normally, the mechanical properties of the lung especially, but also the chest wall and diaphragm may change between two PEEP-levels as indicated by a change in $C_{TOT}$ between the first and the second PEEP level. When such a change is detected in $C_{TOT}$ between the first and the second PEEP level, inflection and deflection points may be determined or calculated as described below.

In a particular example, at certain tidal volumes, the transpulmonary pressure difference between two PEEP levels may be calculated as $$\Delta P_{TP} = (\Delta Paw1 + \Delta Paw2)/2 \times EI/E_{TOT} \quad (11)$$

Where ΔPaw1 is the inspiratory plateau pressure minus the end-expiratory pressure at the first PEEP level and ΔPaw2 is the inspiratory plateau pressure minus the end-expiratory pressure at the second PEEP level.

Thus, the sum of the breath-by-breath volume increase following a step change in PEEP is the total lung volume change caused by an increase in transpulmonary pressure equal to the PEEP change, and lung compliance is $$C_L = \Delta EELV / \Delta PEEP \quad (12)$$

ΔPEEP is directly determined from measurements of the expiratory pressure transducer 133 at the first and second PEEP level. ΔEELV is also determinable from spirometric measurements as described above, preferably by spirometry based on measurements of the breathing apparatus' flow transducers. Having thus determined $C_L$ from equation (12), $\Delta P_{TP}$ is determined from equation (10). ΔPaw is advantageously in embodiments determined from measurements of the breathing apparatus, namely the inspiratory pressure transducer 113. $E_{TOT}$ is also determined from measurements of the breathing apparatus, see equations (3) and (6), namely the inspiratory flow transducer 112 and the inspiratory pressure transducer 113. Thus $\Delta P_{TP}$ is determined based on these calculations without the need of measuring oesophagal pressure. Determining $C_L$, such as by equation 12, and thus $\Delta P_{TP}$ has hitherto not been possible in such an advantageous, convenient, patient safe and cost-effective way.

Identification of Lower and Upper Inflection Points of Non-Linear P/V Curves

As mentioned above, if $C_{TOT}$ at the PEEP level after changing PEEP has changed from the $C_{TOT}$ at the first PEEP level before the change, this indicates that either the lung and/or the chest wall compliance is non-linear. A more precise identification of the level of change of compliance, a lower inflection point, where the second PEEP level $C_{TOT}$ has increased, may be performed by making smaller PEEP level changes and/or by reducing the tidal volume. An upper deflection point, where the second $C_{TOT}$ has decreased compared to the first PEEP level can be identified more precisely in the same way. Combining small PEEP-steps and/or small tidal volumes with equation 11, makes it possible to identify the pressure-volume curve for the lung over the total lung capacity.

In an embodiment, when $C_{TOT}$ changes between PEEP levels, i.e. when non-linear conditions are present, transpulmonary pressure at the first PEEP level ($Vt_{PEEP1}$) is identified by a procedure where a stepwise increase in PEEP is performed until the sum of the stepwise obtained ΔEELV (ΣΔEELV) is equal or close to the tidal volume at the first PEEP level ($Vt_{PEEP1}$): $\Sigma\Delta EELV = Vt_{PEEP1}$ The PEEP level where this ΣΔEELV is obtained is denominated lung compliance PEEP ($PEEP_{CL}$) Lung compliance for the tidal volume at the first PEEP $CL_{VtPEEP1}$ is calculated as $$C_{LVtPEEP1} = \Sigma\Delta EELV/(PEEP_{CL} - PEEP_1)$$

and the transpulmonary pressure of the tidal volume of the first level PEEP is calculated as $$\Delta P_{TPVtPEEP1} = \Delta Paw \times ELVtPEEP11/ETOTVtPEEP1 \quad (13)$$

At tidal ventilation at the highest PEEP level ($PEEP_{PEAK}$), that is deemed possible to use for patient safety reasons, such as limited to avoid baro- and volotrauma, the $C_L$ above this PEEP level ($C_{L_{PEAK}}$) cannot be measured as such. However, the difference in end-inspiratory lung volume (ΔEILV) can be estimated based on the assumption that $C_{TOT}$ at the second highest PEEP level ($C_{TOT_{SH}}$) is related to the ΔEELV measured between the second highest and the highest PEEP level as CTOT at tidal ventilation at the highest PEEP level ($C_{TOT_{PEAK}}$) relates to the end-inspiratory volume difference:

$$C_{TOT_{SH}}/\Delta EELV = C_{TOT\ PEAK}/\Delta EILV$$

which rearranged gives $$\Delta EILV = C_{TOT_{PEAK}} \times \Delta EELV / C_{TOT_{SH}} \quad (14)$$

and $C_{L_{PEAK}}$ can be calculated either by regarding the difference in ΔPaw at $PEEP_{PEAK}$ and $PEEP_{SH}$ ($\Delta Paw_{PEAK-SH}$) as a corresponding change in transpulmonary pressure as obtained by a PEEP change $$C_{L_{PEAK}} = \Delta EILV / \Delta Paw_{PEAK-SH} \quad (15)$$

or as $$C_{L_{PEAK}} = \Delta EILV / \Delta PEEP_{PEAK-SH}$$

where the largest pressure difference of $\Delta Paw_{PEAK-SH}$ or $\Delta PEEP_{PEAK-SH}$ is selected for the calculation.

The transpulmonary pressure at the highest PEEP level $P_{TP_{PEAK}}$ is then calculated by equation (10) as $$P_{TP_{PEAK}} = \Delta Paw_{PEAK} \times E_{L_{PEAK}} / E_{TOT_{PEAK}} \quad (16)$$

Figure 6:
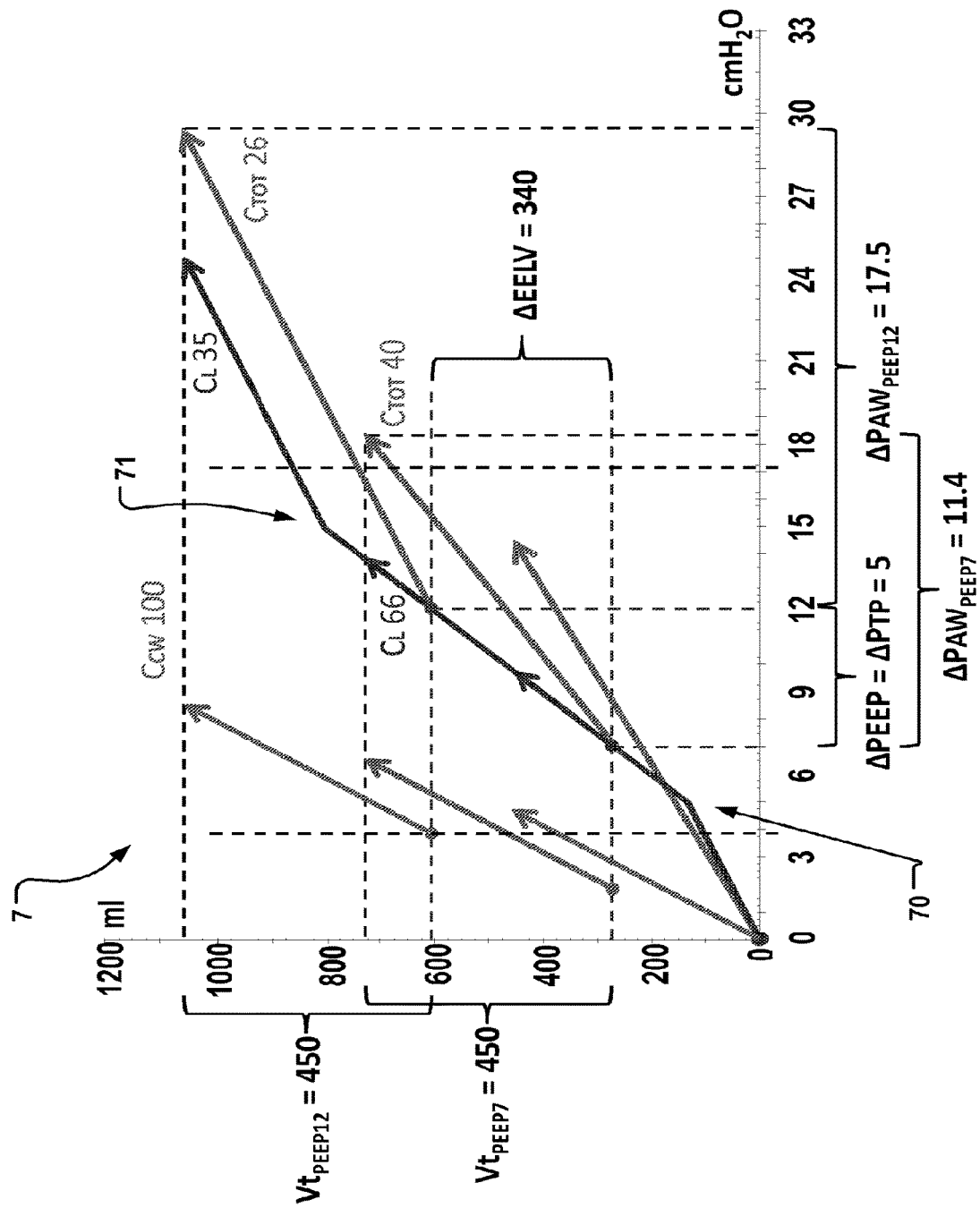
FIG. 6 is a schematic pressure/volume graph of an example of a patient with non-linear compliance conditions.

FIG. 6 is a schematic pressure/volume graph of an example of a patient with non-linear compliance conditions and are given as illustrative examples when implementing the above described system and method.

FIG. 6 is a schematic graph 7 of a patient with linear chest-wall compliance (here 100 ml/cmH$_2$O) and a non-linear lung compliance, with a $C_L$ of 26 ml/cmH$_2$O below 5 cmH$_2$O, the lower inflection point 70 and a $C_L$ of 66 ml/cmH$_2$O between 5 and 15 cmH$_2$O, and a $C_L$ of 26 ml/cmH$_2$O above 15 cmH$_2$O, the upper inflection point 71. Corresponding total compliance values are 20, 40 and 20 ml/cmH$_2$O in the three ranges, respectively.

For correct determination of the transpulmonary pressure during the tidal volume at zero PEEP, the PEEP should be increased until ΔEELV is equal to the tidal volume (450 ml), which in this case would have been achieved increasing PEEP to just above 9 cmH$_2$O. At the highest safe PEEP level the transpulmonary pressure can be calculated by determination of the end-inspiratory lung volume difference between the tidal volume at 7 and 12 cmH$_2$O (ΔEILV), which is calculated according to equation (14) as ΔEILV=26×340/40=221 ml(=$C_{TOT}$×ΔEELV/$C_{TOT}$)

The change in transpulmonary pressure causing this volume change is the difference in ΔPaw of the tidal volume at 12 and 7 cmH$_2$O in PEEP=17.5−11.4=6.1 cmH$_2$O.

The $C_L$ of the tidal volume at the highest PEEP level is calculated according to equation (15):

221/6.1=36 ml/cmH$_2$O ($C_L$=ΔEILV/ΔPEEP)

The transpulmonary pressure of that tidal volume is calculated according to equation (16):

17.5 cmH$_2$O×26/36=12.6 cmH$_2$O
($Ptp$=Δ$Paw_{PEEP12}$×$E_{L_{PEEP12}}$/$E_{TOT_{PEEP12}}$)

Indirect Determination of Chest Wall/Diaphragmatic Elastance ($E_{CW}$)

When both the total respiratory system stiffness, Etot, and the lung stiffness, El, have been determined by the above described method, the stiffness of the chest wall/diaphragm can be determined indirectly as $$E_{CW}=E_{TOT}-E_L \quad (17)$$

This calculation is sensitive to the conditions under which the $E_{TOT}$ has been obtained, as an underestimation of $E_{TOT}$ leads to an overestimation of $E_L$. To avoid this, $E_{TOT}$ may be measured under true static conditions, i.e. both the end-inspiratory and the end-expiratory pressure should be measured after an end-inspiratory/end-expiratory pause of substantial duration (>4 seconds) to release visco-elastic forces and identify an intrinsic PEEP.

Figure 7:
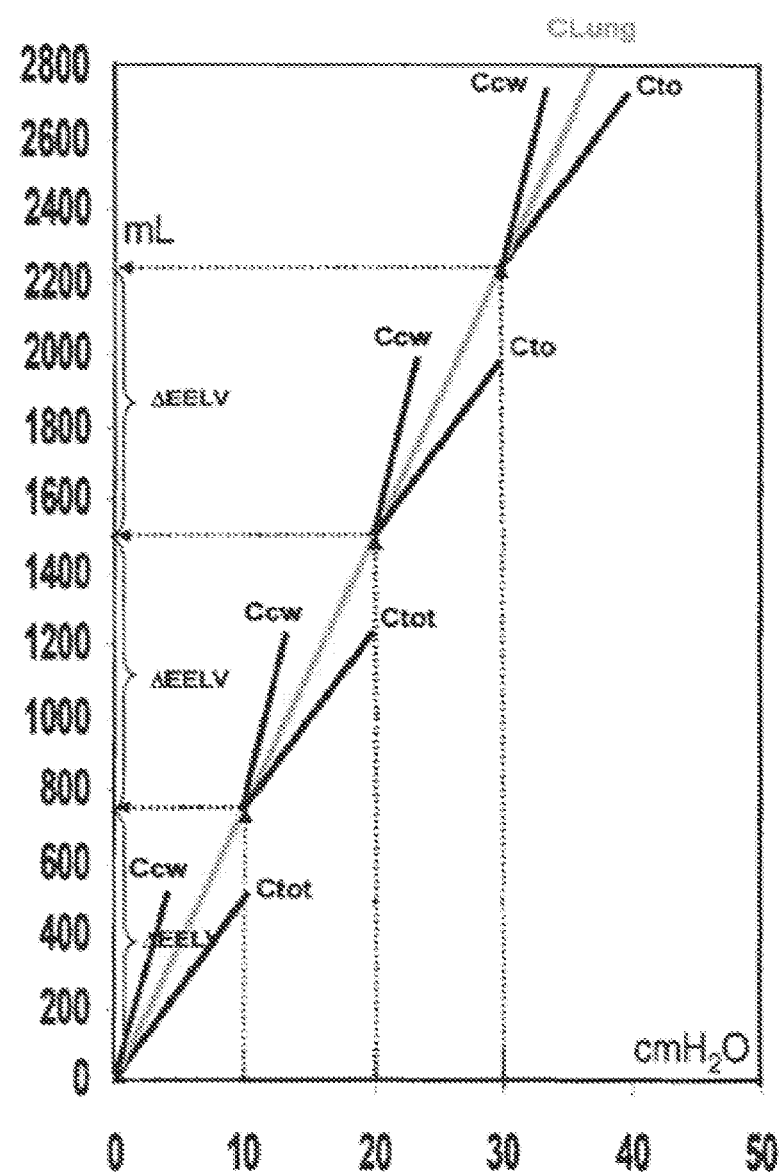
FIG. 7 is a pressure/volume graph of the total respiratory system and chest wall at different PEEP levels.

FIG. 7 is a pressure/volume graph 6 of the total respiratory system ($C_{TOT}$) and chest wall ($C_{CW}$) at different PEEP levels. The schematic graph 6 of tidal P/V curves of the total respiratory system and chest wall is shown at 0, 10, 20 and 30 cmH$_2$O PEEP. As the P/V-curve of the lung consist of the difference of P/V curves of the total respiratory system and chest wall, the start of tidal P/V curves are positioned along the P/V curve of the lung. Lung compliance is determined as ΔEELV/ΔPEEP, in this case 750/10=75.

A method of online adjusting a PEEP level based on a transpulmonary pressure (Ptp) determined according to the above method comprises limiting PEEP to a lower level when lower transpulmonary pressures to protect the lung from injury.

In unhealthy lungs, some air sacs of the lung may collapse. In those collapsed sacs, gas cannot enter or leave them, thus preventing gas exchange through the collapsed air sacs. The ventilator 1 may supply a higher concentration of oxygen in order to provide proper blood oxygenation. In addition, or alternatively, the ventilator 1 may supply an adjusted positive end-expiratory pressure (PEEP) to maintain airways open, based on the aforementioned determined transpulmonary pressure. For instance, by increasing the transpulmonary pressure, collapsed air sacs will start to recruit. When the collapsed air sacs start to open up, they are again available for alveolar gas exchange and the pressure at which the recruitment happens is called the critical opening pressure. The PEEP level is selected to prevent collapse during expiration by identifying a lower inflection point as described above. It is avoided to increase the transpulmonary pressure such that overinflation is avoided. Overinflation may be dangerous for the patient since it may cause undesired lesions in the lung tissues.

A desired transpulmonary pressure may be adjusted accordingly and controlled by repeating the afore described PEEP step manoeuvre.

Setting said breathing apparatus in the second mode of operation (PEEP step) may be selectable from a user interface of said breathing apparatus. The control unit may be adapted to automatically determine said transpulmonary pressure upon said user initiation. Further, the automatic determination may be made during assisted and/or controlled ventilation of said patient by said apparatus. This automatic determination may be made intermittently during the assisted and/or controlled ventilation. The manoeuver may be made at pre-defined time intervals.

The number of breathing cycles in the second mode of operation before being able to determine the transpulmonary pressure is at least one. The closer to an equilibrium the PEEP has adjusted itself to the desired PEEP, the more precise the determined value is. Thus, a single breath in the second mode of operation may be sufficient under certain circumstances. Usually, the second mode of operation will be performed over a plurality of breathing cycles before the transpulmonary pressure is calculated or determined or a value therefore provided.

Animal Studies for Verification

Animal studies were performed to demonstrate the feasibility, effect and efficiency of transpulmonary pressure determination as described herein. The effects of a stepwise increase in PEEP on lung volume and esophageal pressure were analyzed breath by breath. In addition to the demonstration of the measurement principle, also the influence of lung and chest wall mechanics on lung inflation by PEEP were analyzed. An explanation of the physiological and anatomical relationship underlying the effect and efficiency of transpulmonary pressure determination is also given below. The physiological background for the measurement has been found to be the phenomenon that by cohesion between the visceral and parietal pleura, the lung is pulled out against its recoil to the inner volume of the thoracic cavity and the thoracic wall is pulled in to a balancing pressure/volume level. At atmospheric end-expiratory pressure, this results in a positive transpulmonary pressure in spite of zero airway pressure. As described above, lung compliance is be determined as DEELV/DPEEP and transpulmonary pressure calculated as the airway pressure times the total respiratory system compliance divided by the lung compliance. This method is below called "Lung Barometry".

The studies were performed on pigs which were anesthetized and sacrificed and experiments were performed ex vivo. Tracheal and esophageal pressures were measured and changes in end expiratory lung volume determined by spirometry as the cumulative inspiratory-expiratory tidal volume difference. Studies were performed with different PEEP-steps and body positions and with varying abdominal load.

The study was approved by the Committee for Ethical Review of Animal Experiments in Gothenburg, Sweden, and performed in accordance with National Institutes of Health guidelines. Fourteen pigs (28-33 kg) were studied. For anesthesia, the animals were premedicated using 15 mg/kg ketamine (Ketalar, Park-Davis, Sweden) and 0.3 mg/kg midazolam (Dormicum, Roche, Switzerland) intramuscularly. General anesthesia was induced with 6 mg/kg pentobarbital sodium (Apoteksbolaget, Sweden), followed by hourly infusions of 4 mg/kg and 25 µg/kg fentanyl (Fentanyl Pharmalink, Pharmalink, Sweden). Muscle relaxation was achieved by 0.15 mg/kg pancuronium (Pavulon, Organon, Sweden) as a bolus. The pigs were intubated with an 8-mm endotracheal tube (ETT). Mechanical ventilation was performed using a Servo 300 ventilator (Siemens-Elema, Sweden), volume-controlled mode (VCV), TV 10 ml/kg, and inspiratory oxygen fraction of 0.21.

Tracheal airway and esophageal pressure was measured via a pressure line introduced through the ETT, which was connected to a standard pressure receptor for intravascular measurements (PVB Medizintechnik, Germany). Esophageal pressure was measured with a balloon catheter positioned at the lower part of the esophagus. Correct positioning was verified by a rib cage compression test according to Baydur A, Behrakis P K, Zin W A, Jaeger M, Milic-Emili J. A simple method for assessing the validity of the esophageal balloon technique. Am Rev Respir Dis. 1982 November; 126(5):788-91. Ventilatory flow and volume were measured at the Y-piece with a D-lite side stream spirometer connected to an AS/3 multi-module monitor (GE Healthcare, Helsinki, Finland).

For electric impedance tomography (EIT) an elastic belt with sixteen electrodes was placed around the chest wall and connected to the EIT device (Drager, Germany). EIT data were generated by application of electrical currents of 5 mA, 50 kHz with measurements of voltage differences between neighboring electrode pairs in a sequential rotating process, where a complete scan was sampled at 25 Hz. The scan slice has an estimated thickness of 5-10 cm. The electrodes were positioned at a level corresponding to the 5th intercostal space. This level was chosen in accordance with previous findings, where tidal amplitudes of the impedance changes were least affected by increased PEEP. Global electrical impedance end-expiratory level was calibrated vs FRC measured with $N_2$ washin/washout technique. Tidal impedance changes were calibrated by changing tidal volume in steps of 100-200 ml.

End-expiratory lung volume (EELV) was measured using a modified technique for nitrogen washout/washin according to Olegard C et al, "Estimation of functional residual capacity at the bedside using standard monitoring equipment: a modified nitrogen washout/washin technique requiring a small change of the inspired oxygen fraction.", Anesth Analg. 2005 July; 101(1):206-12.

End-expiratory lung volume increase ($\Delta$EELV) following a PEEP step ($\Delta$PEEP) was spirometrically determined by addition of the inspiratory-expiratory tidal volume difference of the breaths needed for establishing the new PEEP level. This determination was done using the Servo 300 spirometry. Also, the $\Delta$EELV was determined using the change in end-expiratory impedance ($\Delta Z$) following a PEEP step. The change in impedance was converted to ml by using the mean value of the $\Delta Z$/ml at the first and second PEEP level.

The tidal variation in esophageal pressure ($\Delta$PES) was determined as PESEIP−PESEE, where PESEIP is the end-inspiratory esophageal plateau pressure and PESEE the end expiratory esophageal pressure. The tidal transpulmonary pressure variation ($\Delta$PES) was calculated as the $\Delta$PAW−$\Delta$PES. The tidal transpulmonary pressure variation ($\Delta$PTP) was calculated as the $\Delta$PAW−$\Delta$PES.

Total respiratory system compliance (CTOT) was calculated as the VT/$\Delta$PAW, where VT is the tidal volume. Total respiratory system elastance (ETOT) was calculated as 1/CTOT. Chest wall compliance (CCW) was calculated as VT/$\Delta$PES. Chest wall elastance (ECW) was calculated as 1/CCW. Lung elastance (EL) was calculated as ETOT−ECW and lung compliance as 1/EL.

The driving pressure related to the PEEP step induced inflation ($\Delta$PAW$\Delta$PEEP) of the respiratory system was calculated as $\Delta$EELV×ETOT. The end-expiratory increase in esophageal pressure related to the PEEP step induced infla-tion ($\Delta$PES$\Delta$PEEP) of the respiratory system was calculated as $\Delta$EELV×ECW. The end-expiratory increase in transpulmonary pressure related to the PEEP step induced inflation ($\Delta$PTP$\Delta$PEEP) of the respiratory system was calculated as $\Delta$EELV×ETOT−$\Delta$EELV×ECW.

Predicted $\Delta$EELV was calculated as $\Delta$PEEP/EL, $\Delta$PEEP/ECW and as $\Delta$PEEP/ETOT.

Experimental Procedure

In Vivo

Ventilation was set to volume control mode, tidal volume 10-12 ml/kg body weight, respiratory rate 10, inspiratory time 30%, end-inspiratory pause 10%. A step increase in PEEP from 0 $cmH_2O$ to 12 $cmH_2O$ was performed. After the expiratory tidal volume returned to the zero PEEP level, or after >80 seconds, PEEP was reduced in one step to zero $cmH_2O$.

As the main aim of this study was to study respiratory mechanics and not gas exchange, the animal was then sacrificed by an overdose of pentobarbital. This eliminated the cardiac related pressure variations in the pressure signal resulting in an ex vivo respiratory mechanics lung model.

Ex Vivo

The duration of the ex vivo experimental procedure was around 120 minutes.

1. EIT calibration by changing tidal volume stepwise from baseline 250 to 300, to 500 and to 700 ml.
2. Pig positioned horizontal supine.
2:1. Tidal volume calibration of EIT
2:2. PEEP up from 0 to 4 $cmH_2O$ and back to 0 $cmH_2O$
2:3. PEEP up from 0 to 8 $cmH_2O$ and back to 0 $cmH_2O$
2:4. PEEP up from 0 to 12 $cmH_2O$ and back to 0 $cmH_2O$
3. Pig positioned horizontal supine.
3:1. Abdomen loaded with sandbags weighing 8 kg.
3:2 Tidal volume calibration of EIT
3:3. PEEP up from 0 to 4 $cmH_2O$ and back to 0 $cmH_2O$
3:4. PEEP up from 0 to 8 $cmH_2O$ and back to 0 $cmH_2O$
3:5. PEEP up from 0 to 12 $cmH_2O$ and back to 0 $cmH_2O$
3:6 Weight removed
4. Pig positioned horizontal supine.
4:1. Operating table positioned reverse Trendelenburg with an angle of 30°.
4:2. Tidal volume calibration of EIT
4:3. PEEP up from 0 to 4 $cmH_2O$ and back to 0 $cmH_2O$
4:4. PEEP up from 0 to 8 $cmH_2O$ and back to 0 $cmH_2O$
4:5. PEEP up from 0 to 12 $cmH_2O$ and back to 0 $cmH_2O$
4:6. Operating table returned to horizontal position.
5. Tidal volume calibration of EIT
6. PEEP up from 0 to 12 $cmH_2O$ and back to 0 $cmH_2O$ Results Lung and chest wall mechanics for the 13 ex vivo pig experiments at baseline in horizontal position are presented in Table 1.

TABLE 1

Baseline, horizontal position mechanics

| Horizontal | $E_{TOT}$ | Ecw | $E_{Lung}$ | $E_L/E_{TOT}$ |
|---|---|---|---|---|
| P1 | 142.7 | 20.0 | 122.6 | 0.86 |
| P2 | 43.9 | 6.6 | 37.3 | 0.85 |
| P3 | 41.1 | 15.6 | 25.5 | 0.62 |
| P4 | 53.3 | 16.3 | 37.0 | 0.69 |
| P5 | 46.6 | 23.7 | 22.9 | 0.49 |
| P6 | 105.0 | 12.0 | 93.0 | 0.89 |
| P7 | 65.7 | 14.4 | 51.3 | 0.78 |
| P8 | 35.6 | 20.5 | 15.1 | 0.42 |
| P9 | 81.0 | 15.4 | 65.6 | 0.81 |
| P10 | 36.0 | 13.7 | 22.4 | 0.62 |

TABLE 1-continued

Baseline, horizontal position mechanics

| Horizontal | $E_{TOT}$ | Ecw | $E_{Lung}$ | $E_L/E_{TOT}$ |
|---|---|---|---|---|
| P11 | 35.0 | 14.0 | 21.0 | 0.60 |
| P12 | 73.2 | 18.7 | 54.5 | 0.74 |
| P13 | 37.9 | 14.5 | 23.3 | 0.62 |
| Mean ± | 57.7 | 16.1 | 41.5 | 0.68 |
| SD | 31.0 | 4.3 | 30.0 | 0.14 |

Figure 8:
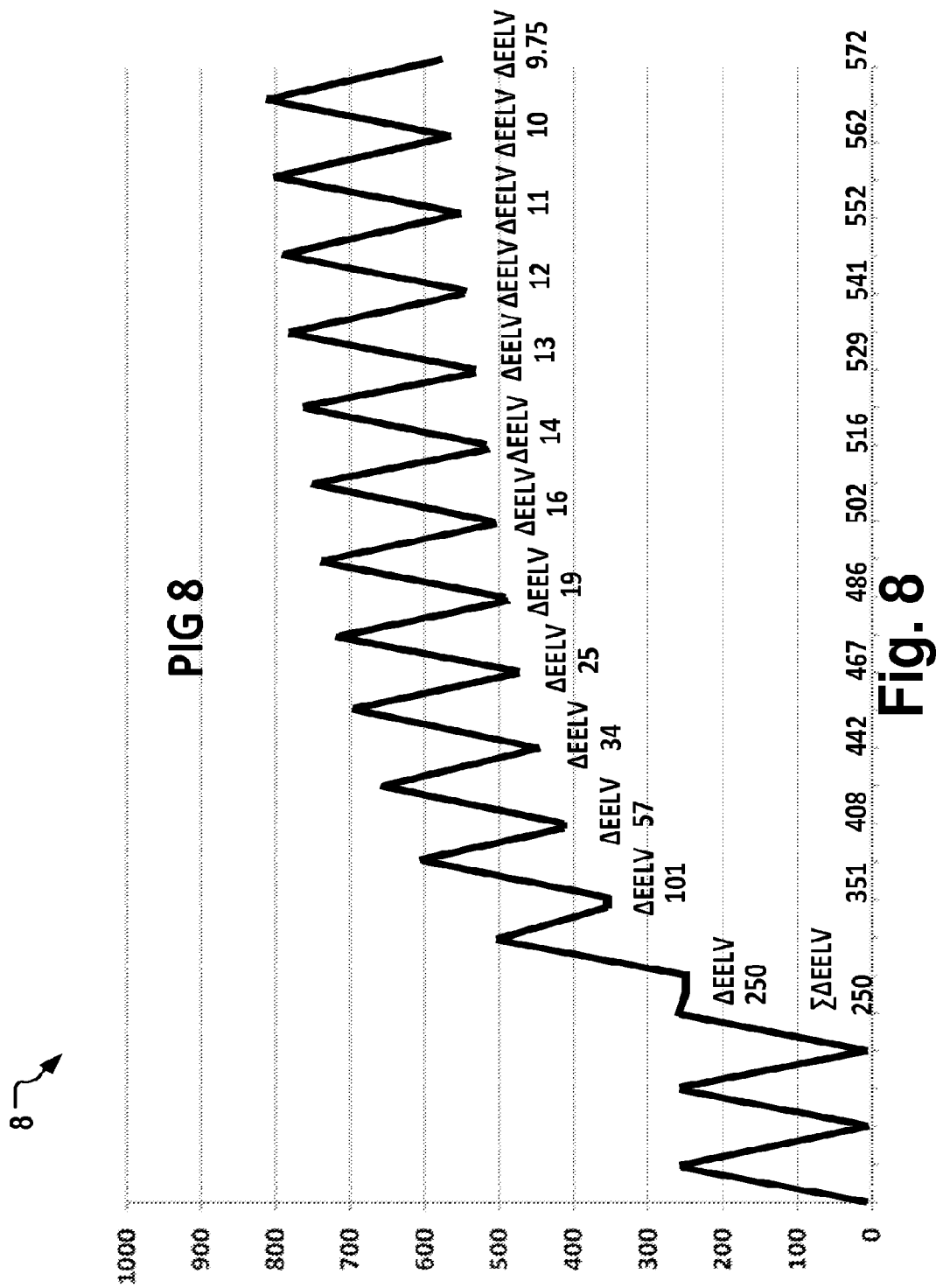
FIG. 8 is a graph 8 illustrating a breath-by-breath increase in end-expiratory lung volume ($\Delta$EELV) during an animal trial for verification of the method.

Successive inflation of the lungs following a PEEP increase in ex vivo pigs in horizontal position, see FIG. 8. In FIG. 8, the breath-by-breath increase in end-expiratory lung volume (ΔEELV) following a change in PEEP is increased from 0 to ~12 cmH$_2$O in a pig at zero PEEP, reverse Trendelenburg, with a total respiratory system elastance of 41.7 cmH$_2$O/L, a chest wall compliance of 20.4 cmH$_2$O/L and a lung compliance of 20 cmH$_2$O/L and a tidal volume of 250 ml. Note, that the first expiration build-up of lung volume is equal to the tidal volume, 250 ml. In comparison the calculated first expiratory increase in lung volume should have been ΔPEEP/ETOT, i.e. 11/0.042=264 ml.

Figure 9:
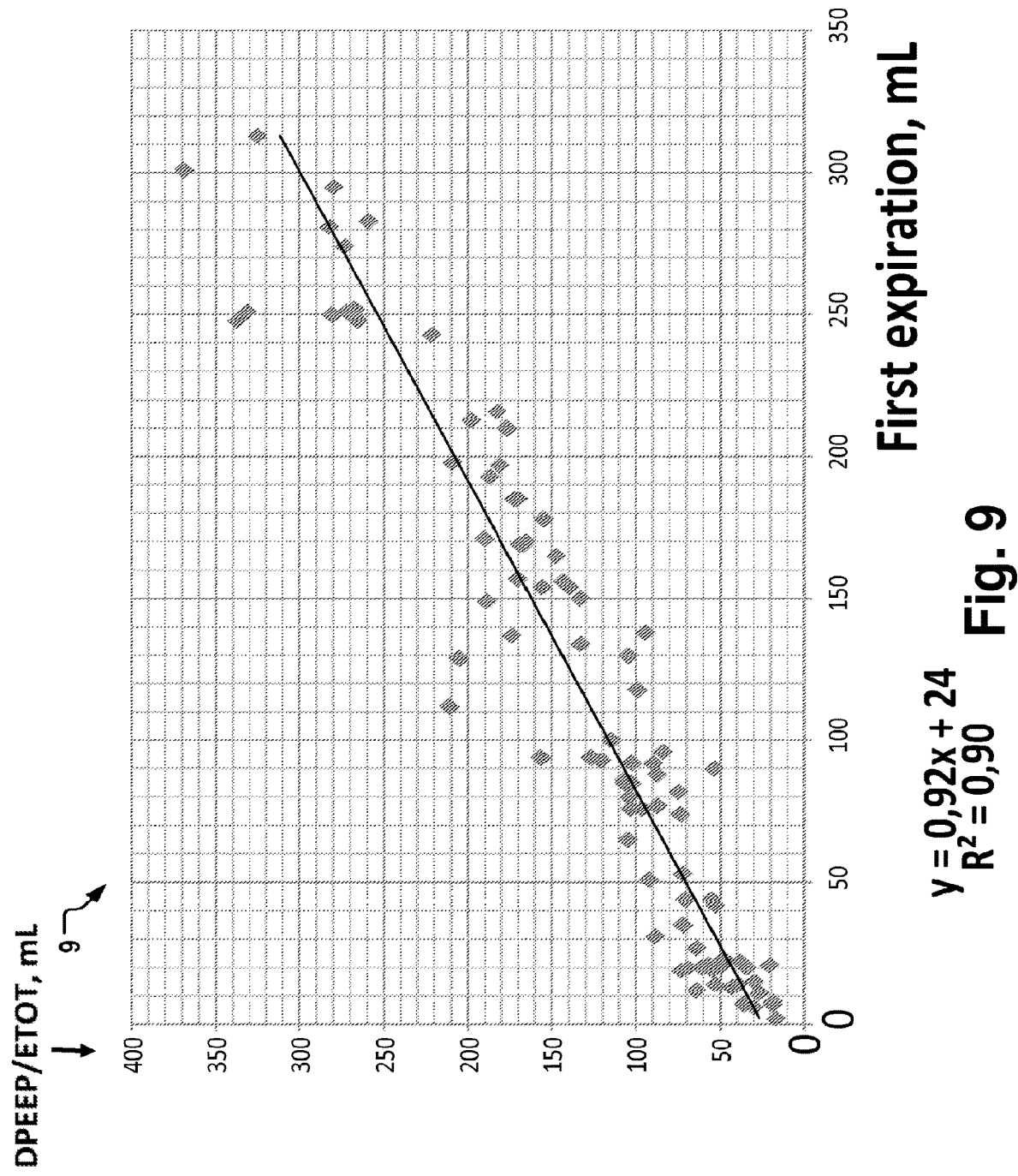
FIG. 9 is a graph 9 illustrating a correlation between the end-expiratory volume increase after the first expiration after increasing PEEP.

The increase in EELV after the first breath following the PEEP increase was closely correlated to ΔPEEP/ETOT$_{zeroPEEP}$, $r^2$=0.90, where ETOT$_{zeroPEEP}$ is the total respiratory system elastance measured at 0 cmH$_2$O PEEP prior to the PEEP step, see FIG. 9. FIG. 9 is a graph illustrating a correlation between the end-expiratory volume increase after the first expiration after increasing PEEP.

Figure 10:
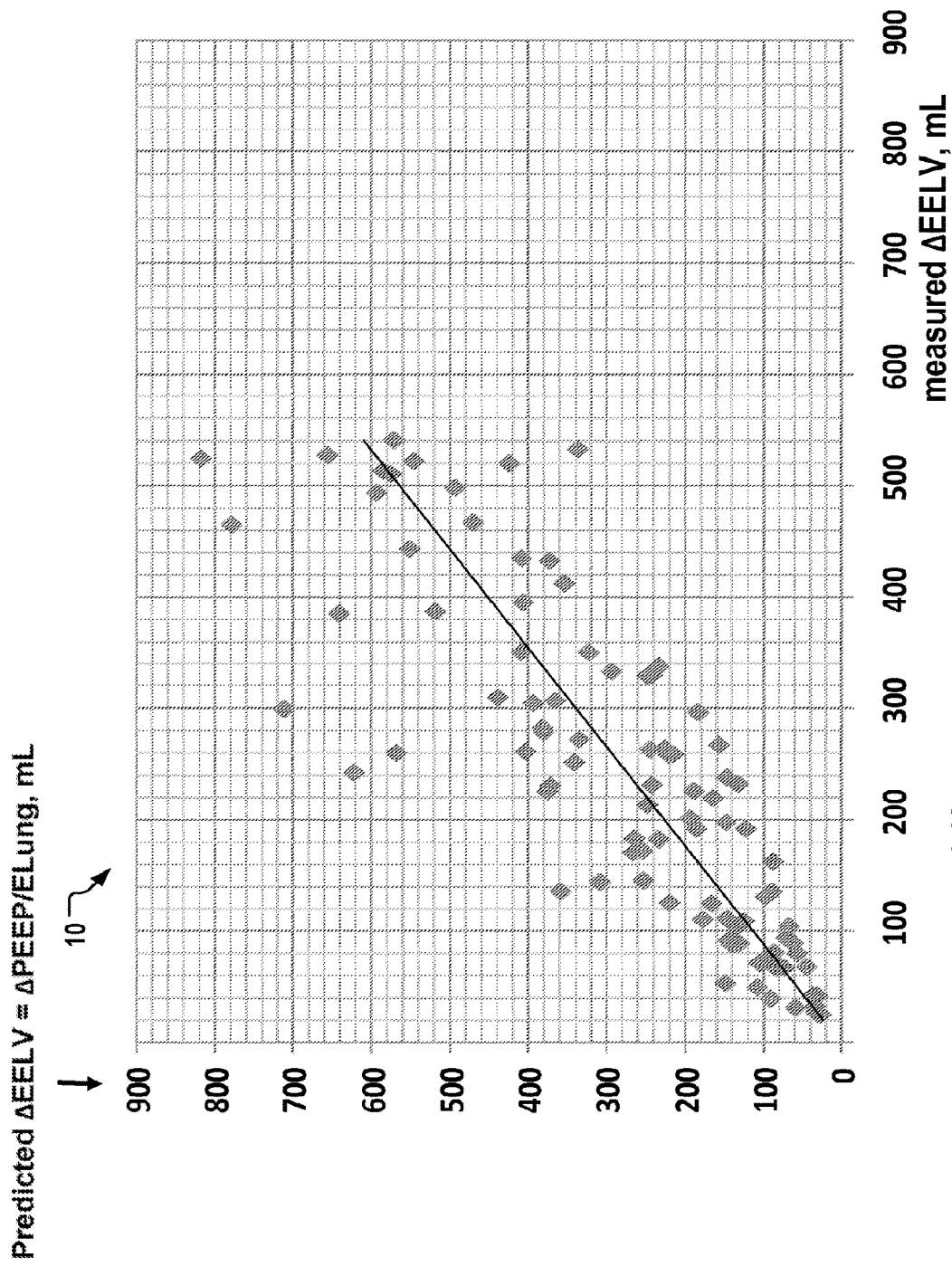
FIG. 10 is a correlation plot 10.

The correlation between the measured ΔEELV using spirometry and ΔEELV predicted from the ΔPEEP/EL$_{calVT}$ was $r^2$=0.70, y=1.13x, where EL$_{calVT}$ is the lung elastance calculated from tidal changes in airway and esophageal pressures obtained from the calibration breaths performed before the PEEP change at the tidal volume closest to the ΔEELV which occurred following the PEEP change, see FIG. 10. FIG. 10 is a correlation plot of measured end-expiratory lung volume change using spirometry and the end-expiratory lung volume change calculated from lung elastance and the PEEP change (ΔPEEP/EL).

If prediction of ΔEELV following a PEEP step was performed from values of total elastance (ETOT), ΔPEEP/ETOT results in predicted values being around 0.73 times the spirometrically measured ΔEELV ($r^2$=0.84, y=0.73x). Prediction of ΔEELV using chest wall elastance (ECW), i.e. ΔPEEP/ECW results in predicted lung volume changes being around 2.3 times the measured ΔEELV ($r^2$=0.61, y=2.31 x).

The Driving Pressure of a PEEP Induced Respiratory System Inflation

Figure 11:
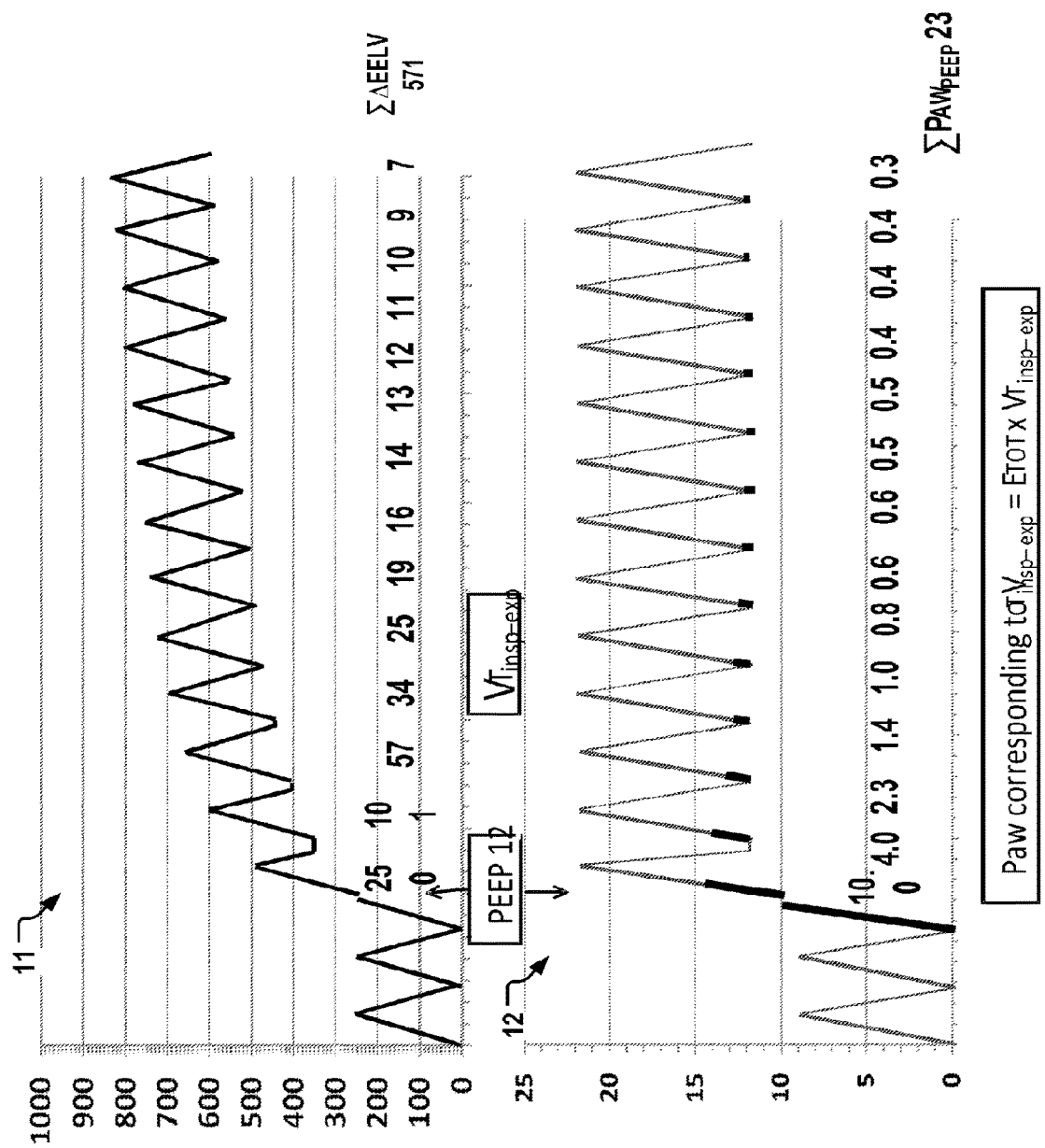
FIG. 11 are shows graphs 11, 12 of Volume and driving pressure during a PEEP step.

The driving pressure of a PEEP induced inflation of the respiratory system was calculated as ΔEELV×ETOT. This cumulative driving pressure can be considered to be exerted during the preceding inspiration of each breath involved in establishing the new end-expiratory pressure-volume equilibrium as shown in FIG. 11. FIG. 11 shows graphs of Volume and driving pressure during a PEEP step of 12 cmH$_2$O in pig 8 Supine. The Upper panel in FIG. 11 shows the spirometric tracing of lung volume increase breath by breath. In the lower panel of FIG. 11, the driving pressure is indicated by thicker lined bars of the inspiratory airway pressure increase correlating to the increase in lung volume for each breath.

Changes in Esophageal Pressure During a PEEP Step

Tidal variations in esophageal pressure (ΔPES) before and after a PEEP step did not change substantially and was 5.8±2.2 cmH$_2$O at zero PEEP and 5.5±2.2 cmH$_2$O, 5.1±1.7 cmH$_2$O, and 5.1±1.6 cmH$_2$O at a PEEP of 4, 8 and 12 cmH$_2$O respectively. The end-expiratory esophageal pressure (PESEE) increase was closely correlated to the first end-expiratory lung volume increase and the chest wall elastance, ΔEELV1×ECW ($r^2$=0.80, y=0.87x).

After the first expiration, there was no further increase in PESEE in spite of a continuing increase in end-expiratory lung volume. Horizontal position, ΔPEEP12 cmH$_2$O, ΔEELV 580 ml. The end-expiratory esophageal pressure did not increase after the first expiration in spite of a continuing increase in lung volume.

Abdominal Loading

Applying a weight of 8 kg on the upper abdomen resulted in an increase in end-expiratory esophageal pressure (PESEE) from −1.8±2.1 cmH$_2$O to −1.22±3.0 cmH$_2$O. Abdominal loading resulted in an increase in both lung and chest wall elastance from 50.1±36.5 and 17.1±4.5 cmH$_2$O/L to 65.3±33.8 and 29.2±8.9 cmH$_2$O/L respectively. The ratio of lung to total respiratory system elastance (EL/ETOT) was 0.78±0.14 before and 0.70±0.14 after abdominal loading.

Following loading there was no change in the end-expiratory airway pressure, but the end-expiratory esophageal pressure, which immediately increased following the PEEP increase gradually returned the pre-loading level during the experimental sequence.

Reverse Trendelenburg Effects

Tilting of the pig head up 30° resulted in a decrease in end-expiratory esophageal pressure (PES$_{EE}$) to −5.1±2.2 cmH$_2$O. Lung elastance decreased from 50.1±36.5 to 44.5±23.1 cmH$_2$O/L. Chest wall elastance increased from 17.1±4.5 to 19.9±4.0 cmH$_2$O/L. The ratio of lung to total respiratory system elastance (EL/ETOT) after tilting was 0.71±0.1.

Following reverse Trendelenburg positioning, there was no change in the end-expiratory airway pressure, but the end-expiratory esophageal pressure, which immediately decreased gradually returned the pre-tilt level during the experimental sequence.

Discussion

In this ex vivo study of respiratory mechanics it was shown that the lung volume increase, ΔEELV, caused by stepwise raising the end-expiratory pressure involves several breaths even when the resulting ΔEELV is less than a tidal volume. The driving pressure needed to inflate the lung and push the chest wall out is exerted during the inspiratory phase of the breaths involved in establishing a new end-expiratory pressure-volume equilibrium and the driving pressure can be calculated from the size of the volume change and the elastance of the total respiratory system as ΔEELV/ETOT. The end-expiratory pressure esophageal pressure did not further increase after the first expiration after increasing PEEP even though the end-expiratory lung volume continued to increase and the end-expiratory esophageal pressure was negative or minimally positive even at 12 cmH$_2$O of PEEP. The chest wall P/V curves were successively left shifted when PEEP was increased. The ΔEELV following a PEEP increase seems to be predictable from the degree of PEEP increase ΔPEEP and the lung elastance as ΔPEEP/EL.

Breath by Breath Build Up of End-Expiratory Pressure and Volume

The PEEP induced inflation of the respiratory system is signified by the force necessary to inflate the lungs and to push the chest wall to its new end-expiratory pressure-volume equilibrium. This force, the driving pressure, is exerted during the inspiration preceding each of the breaths involved in the build-up of a new end-expiratory pressure and lung volume equilibrium. This is especially evident concerning the first expiration after increasing PEEP, where the volume is closely related to ΔPEEP/ETOT.

The end-expiratory lung volume increase continues breath by breath, and each breath has the driving pressure of the difference between the inspiratory and expiratory tidal volume, the tidal ΔEELV times the elastance of the lung and the chest wall. Thus, the driving pressure needed to establish a new pressure-volume equilibrium is equal to the total change in end-expiratory lung volume times the total respiratory system elastance. The driving pressure of the PEEP step can be regarded as the airway pressure of an ordinary tidal inspiration with a volume equal to the change in end-expiratory lung volume.

A PEEP increase results in a multi-breath, successively decreasing build-up of the end-expiratory lung volume. In the present study, where volume control ventilation was used, the inspiratory tidal volume is constant from before the PEEP change until a new equilibrium is reached. The expiratory tidal volumes, in contrast, change during the course of the PEEP increase. The first expiratory tidal volume after the PEEP increase is lower than the preceding inspiration and equals the ΔPEEP divided by the total respiratory system elastance (ETOT). The following expirations will increase successively until the expiratory tidal volume is equal to the inspiratory tidal volume and a new end-expiratory pressure-volume equilibrium is reached.

Stress Adaptation

No pre-study inflation was used and the stress adaptation was studied during ex-vivo ongoing ventilation without gas exchange. Thus, very time consuming adaptation over 15-30 minutes could be studied. The pronounced plasticity of the respiratory system was shown especially after reverse Trendelenburg positioning and abdominal weight application (see FIG. 8a,b) where the end-expiratory esophageal pressure decreases and increases respectively. During the course of the following experimental procedures (10-20 minutes) with tidal volume calibration and PEEP increase and decrease, end-expiratory esophageal pressure slowly returned to the baseline prior to that the animal was tilted or abdominal weight was applied.

Changes in Esophageal Pressure During PEEP Elevation

Absolute esophageal pressure measurements in supine position may be misleading due to the effects of mediastinal tissue weight upon on the esophageal measurement balloon. As the esophageal pressure is a surrogate measurement of pleural pressure, the end-expiratory esophageal pressure trace at zero PEEP was transpositioned to −5 cmH$_2$O, which is a commonly reported mean pleural pressure. Even at 12 cmH$_2$O PEEP, the transpositioned end-expiratory esophageal pressure remained negative.

An increase in PEEP only marginally changed the end-expiratory esophageal pressure level and the absolute increase in esophageal pressure was limited to the first expiration after the PEEP increase. This is a surprising finding as the increase in lung volume and consequently also in thoracic cavity volume continues for a number of breaths after the first expiration. This lack of further increase in end-expiratory esophageal pressure during ongoing increase in respiratory system volume may be caused by the properties of the thoracic cavity enclosure in a wide sense, including the rib cage and its muscles, the diaphragm and the abdominal wall and the abdominal content, adapting to the volume expansion by merely yielding i.e. stress adaptation.

The abdomen can be regarded as a fluid filled container, with a volume of around 10 liters which in the supine position has a ventro-dorsal height of approximately 15 cm. The abdominal the "surface" area of the abdominal container is approximately 7 dm$^2$. Increasing the end-expiratory lung volume 0.5 l by increasing PEEP results in a surface level lift of 0.7 cm and an end-expiratory esophageal pressure increase with approximately 0.7 cmH$_2$O.

As abdominal wall stress adaption seems to result in a further increase in abdominal surface area, the end-expiratory esophageal pressure increase may be even less. There was very little increase in end expiratory esophageal pressure at zero and 3 cmH$_2$O of PEEP at 5 mmHg of abdominal pressure and no further increase when the abdominal pressure was increased to 10 mmHg. This pattern is even more evident at a PEEP of 8 cmH$_2$O in the study, which resulted in a moderate end-expiratory esophageal pressure increase when an abdominal pressure of 5 mmHg was implemented. The end-expiratory esophageal pressure did not further increase when the abdominal pressure was increased to 10 mmHg, which indicates that abdominal wall yields and abdominal pressure was not transmitted to the thoracic cavity.

The Role of the Diaphragm

The PEEP induced end-expiratory lung volume expansion results in a displacement of the diaphragm and the abdominal content in caudal and lateral direction with very little change of chest wall elastance. In the present study, the esophageal tidal pressure-volume variations showed that the chest wall P/V curve is successively left and parallel shifted with increasing PEEP steps and the P/V curve of each PEEP level have approximately the same slope, which is fully in accordance with stress adaptation of the abdominal wall. This is further supported by the fact that the diaphragm muscle loses its basic end-expiratory tension, maintained during spontaneous breathing and converts to a passive structure during positive pressure ventilation. The end-expiratory tension is determined by the diameter of the rib cage, the length of the diaphragm and the hydrostatic abdominal pressure during controlled ventilation. During spontaneous breathing the diaphragmatic muscle tension, possibly especially the crural (dorsal) portion, prevents the abdominal content to push the dependent diaphragm in cranial direction even if the whole diaphragm is displaced in cranial direction when changing position from standing to supine. This movement is in spontaneous breathing subjects largely equal in non-dependent and dependent regions.

When controlled ventilation is started, the end-expiratory tension of the diaphragm is lost, the diaphragm is moved cranially and the ventro-dorsal diameter of the rib cage decreases as the diaphragm is passively stretched by the force of the hydro-static pressure from the abdomen. The cranial movement of the diaphragm will be most pronounced in the dorsal, dependent region, which is most exposed to the hydro-static pressure of the abdomen and end-expiratory lung volume decreases predominately in the dependent lung regions.

The Role of the Rib Cage

The rib cage is the resilient framework of the thoracic cavity and the lever for action of the respiratory muscles, intercostal and diaphragm. At FRC, the rib cage wants to spring out to a resting position around 700 ml above FRC. In contrast the lung at FRC wants to recoil to below its residual volume, around 500 ml below FRC (Nunn's Applied respiratory physiology. 4$^{th}$ edition, chapter 3, page 48. Butterworth, Heinemann, 1995). These two contra-directional forces results in a mean positive transpulmonary pressure equal to the negative mean pleural pressure, usually around 5 cmH$_2$O. Even though there is no pressure gradient between the alveoli and the ambient room, the whole lung is open even at FRC. Thus, the lung is suspended within the thoracic cavity and if the end-expiratory lung volume is changed by an increase in end-expiratory pressure, the "FRC compliance" can be determined as $\Delta EELV/\Delta PEEP$. This implicates that at any level of end-expiratory pressure above zero, the only force that prevents the lung from recoiling is the end-expiratory pressure maintained by the ventilator. Further, this implies that the rib cage acts as a frame preventing the chest wall and diaphragm from leaning on, or squeezing the lung even at increased PEEP levels. The spring out force of the rib cage can be estimated to be present up to end expiratory lung volumes of levels >4 liters as a PEEP instigated increase in end-expiratory lung volume will be distributed between the rib cage and the diaphragm, which is pushed in caudal direction. If FRC is 2.5 l an increase of lung volume up to 4 liters will expand the rib cage with approximately 0.7 l and the rest of the volume will displace the diaphragm. During controlled ventilation, the end-expiratory lung volume is decreased by 0.5 l in a healthy supine person and much more in patients with respiratory failure, which means that the PEEP can be increased significantly without losing the "spring out force" of the rib cage. We found that the transpositioned end-expiratory esophageal pressure only in a few cases reached atmospheric level even at high PEEP. This further underlines that, at end of expiration, the lung is suspended by the spring out force of the rib cage and the only force preventing its recoil is the end-expiratory pressure of the ventilator. Thus, at end-expiration, the chest wall does not seem to exert a pressure on the lung and only the end-expiratory airway pressure, maintained by the ventilator, prevents the recoil of the lung.

Passive expiration is not a single compartment, but a two compartment phenomenon, with rapid initial flow and a slow final flow. The initial phase of expiration is passive by recoil of the stretched tissues, but at the later part, the expiration is slower, which may be explained by the rib cage springing out or stopping at a higher volume during the last part of expiration. The increase in rib cage diameter will lead to a passive stretching of the diaphragm, which will counteract the cranial movement of the abdominal content. As a result, the expiratory flow is decreasing during the end of expiration, and at static conditions at end-expiration the rib cage is in a spring out state and the diaphragm stretched, which will keep the pleural pressure negative even at increased PEEP levels.

Relation Between Changes in End-Expiratory Pressure ($\Delta PEEP$) and Lung Volume ($\Delta EELV$) During PEEP Elevation It is well known that the increase in end-expiratory lung volume following a PEEP increase cannot be predicted from the size of the PEEP step and the total respiratory system compliance. Prediction of $\Delta EELV$ calculated as the change in end-expiratory pressure divided by the total respiratory system elastance ($\Delta PEEP/ETOT$) in this study resulted in predicted volumes which were only around half of the spirometrically measured $\Delta EELV$ following a PEEP step. Prediction of the change in end-expiratory lung volume calculated as the change in end-expiratory pressure divided by the chest wall elastance ($\Delta PEEP/ECW$) resulted in predicted volumes twice the measured $\Delta EELV$. Prediction of the change in end-expiratory lung volume calculated as the change in end-expiratory pressure divided by the lung wall elastance ($\Delta PEEP/EL$) resulted in predicted volume being fairly closed to measured $\Delta EELV$, ($r^2=0.70$), which indicates that the end-expiratory transpulmonary pressure seems to continue to increase breath by breath also after the first expiration until a new end-expiratory pressure/volume equilibrium is reached, where the increase in end-expiratory transpulmonary pressure equals the change in end-expiratory airway pressure, $\Delta PEEP$.

In summary, a PEEP step results in a marginal build-up of end-expiratory esophageal pressure as the chest wall and abdomen accommodates changes in lung volume by stress adaptation, which is a process with a duration of 10-30 minutes following a PEEP step. Even at fairly high PEEP levels of approximately 12 $cmH_2O$, the end-expiratory esophageal pressure remains negative. The chest wall and diaphragm exert no, or very limited pressure on the lung at end-expiratory pressure-volume equilibrium over a wide range of PEEP levels as a result of the rib cage end-expiratory spring out force, which counteracts the recoil of the lung. The spring out force of the rib cage retains the last part of the expiration and stretches the diaphragm, which limits abdominal hydrostatic pressure influence on the dependent lung.

A Lung Model Analog

Figure 12:
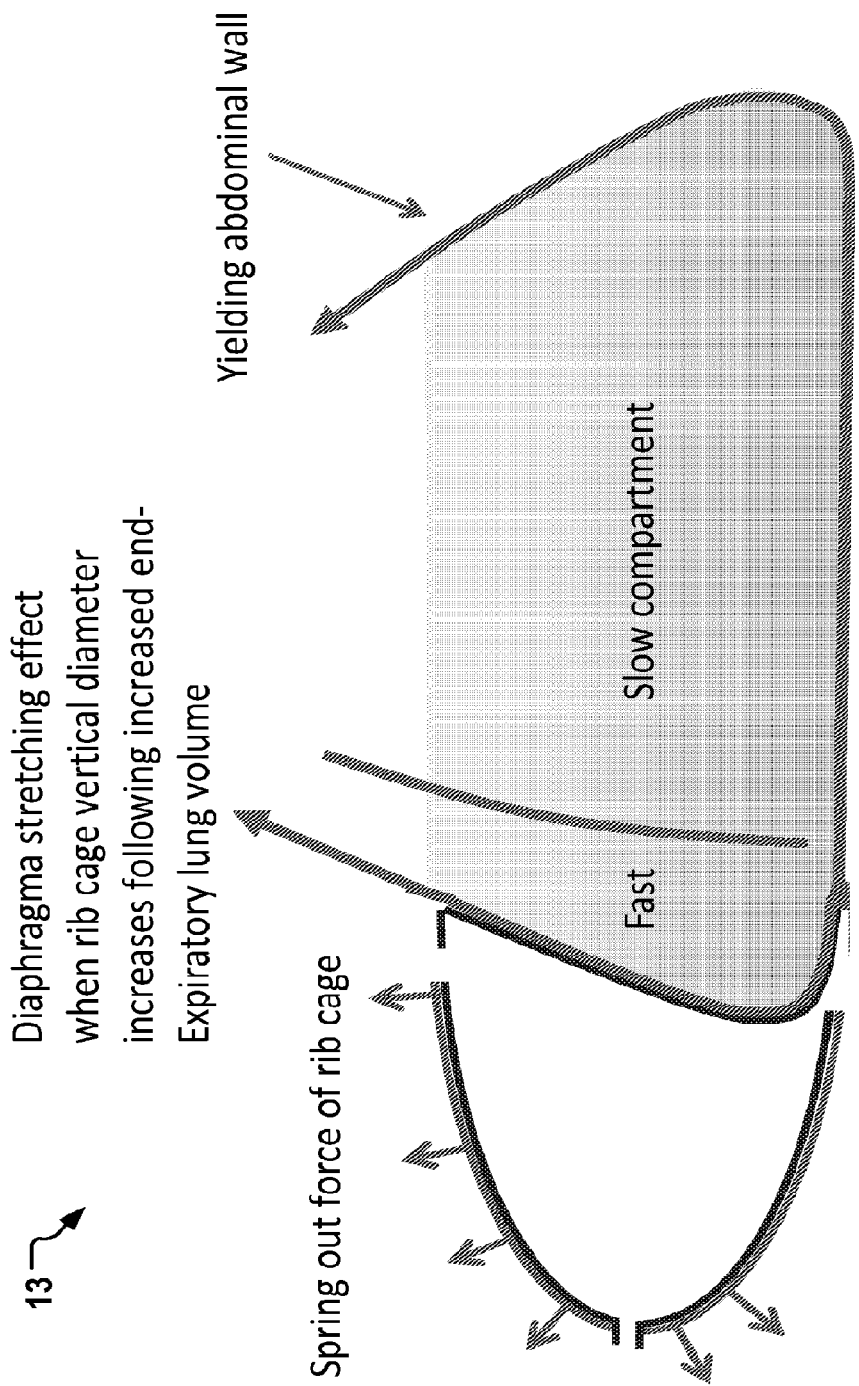
FIG. 12 is a schematic illustration 13 of a lung model.

A lung model covering the behavior of the respiratory system as described in the present study, must encompass a lung with recoil, a rib cage with a spring out force, a fast and a slow abdominal hydraulic compartment with a wall with structural elasticity. In FIG. 12, such a lung model is described. FIG. 12 shows a schematic lung model with lung with recoil and rib cage with a spring out force keeping the lung open at FRC. When the end-expiratory lung volume increases, the vertical diameter of the rib cage increases and the diaphragm is stretched, thereby increasing the tension and the abdominal content is prevented from pressing direct on the lung, especially the dorsal parts. The surface of the slow abdominal compartment is around 7 dm2 and a caudal displacement corresponding to 0.5 L will raise the surface with less than 1 cm and the end-expiratory esophageal (pleural pressure) will increase minimally following such a displacement of the diaphragm. Tidal variations of esophageal pressure will reflect the fast compartment as the inertia of the fluid and organs of the slow compartments will only be involved following a PEEP change.

Clinical Implications

The respiratory mechanical findings of this study indicate that recruitment is a much more time consuming process than previously envisaged, where vital capacity recruitment maneuvers of less than 30 seconds have been regarded as sufficient. Also, a recruitment maneuver affects the chest wall to a high degree and it could be stated that not only the lungs is recruited but to a large extent also the chest wall, which has a plasticity that makes it possible to increase thoracic cavity volume with limited esophageal pressure increase. A PEEP increase seems to result in an opening up of the thoracic cavity, i.e. a caudal displacement of the diaphragm, preferential the non-dependent parts making room for an expansion of non-dependent lung. In this sense the PEEP increase does not primarily result in an opening of previously collapsed dependent lung but rather an expansion of already open non-dependent lung.

Another possibly important clinical implication is the finding that the increase in EELV following a PEEP increase can be predicted from the magnitude of change in PEEP and the lung elastance as $\Delta PEEP/EL$. The correlation coefficient is ($r^2=0.70$) and the equation of the line of is close to 1 ($y=1.13x$). The stress adaptation was related to the size of the PEEP step and lead to a great variability of the results, especially at PEEP steps of 8 and 12 $cmH_2O$. However, our results indicate that lung compliance could be determined without esophageal pressure measurements by measuring the change in end-expiratory lung volume and divide it by the change in end-expiratory pressure, ΔEELV/ΔPEEP, as the PEEP increase induced change in transpulmonary pressure is closely related to the tidal transpulmonary pressure variation of a tidal volume of the same size as the PEEP induced ΔEELV, see FIGS. 13 and 14.

Figure 13:
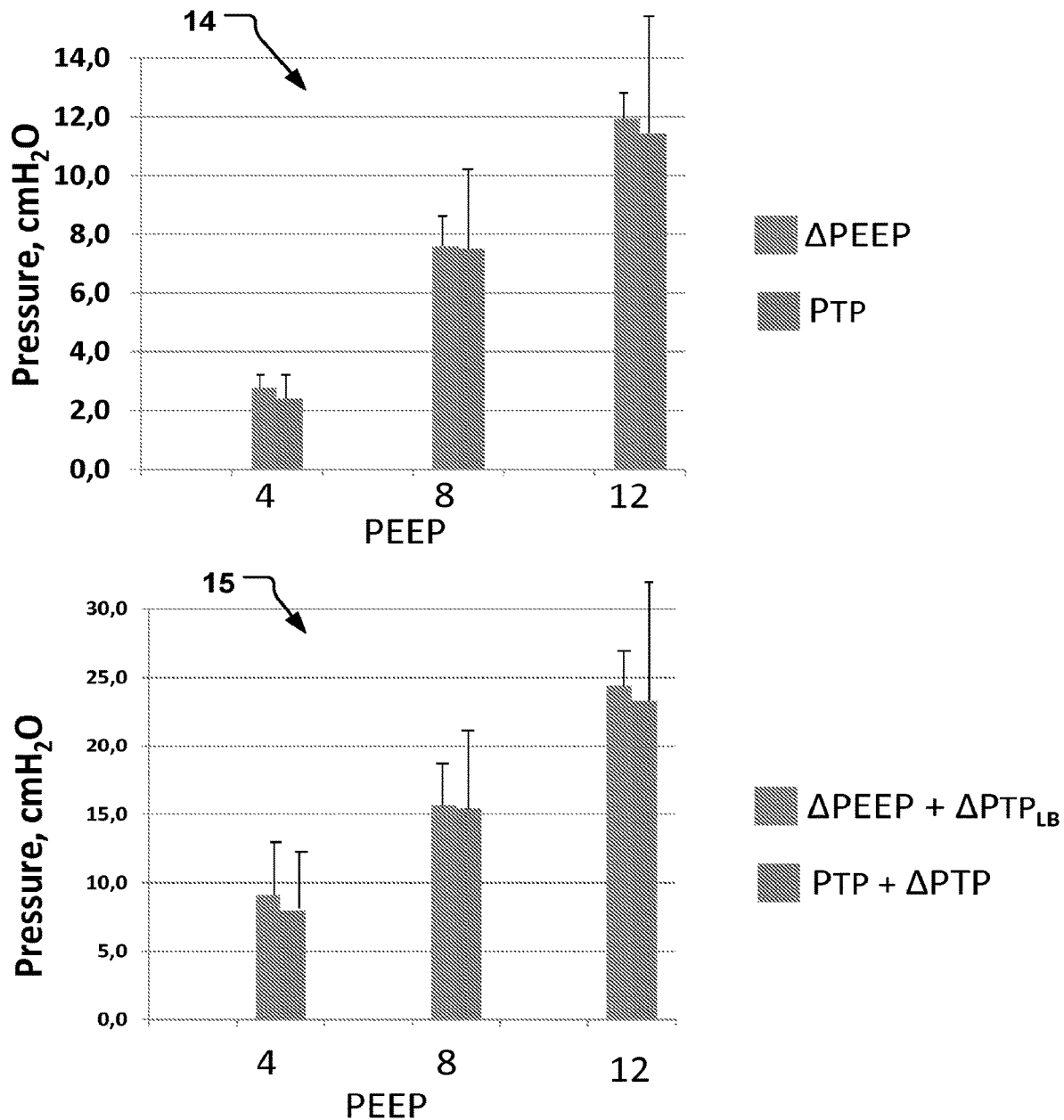
FIG. 13 are diagrams 14, 15 comparing a change in transpulmonary pressure.

FIG. 13 is a diagram comparing the change in transpulmonary pressure of a tidal volume of the same size as the ΔEELV following a PEEP change and the PEEP change.

Figure 14:
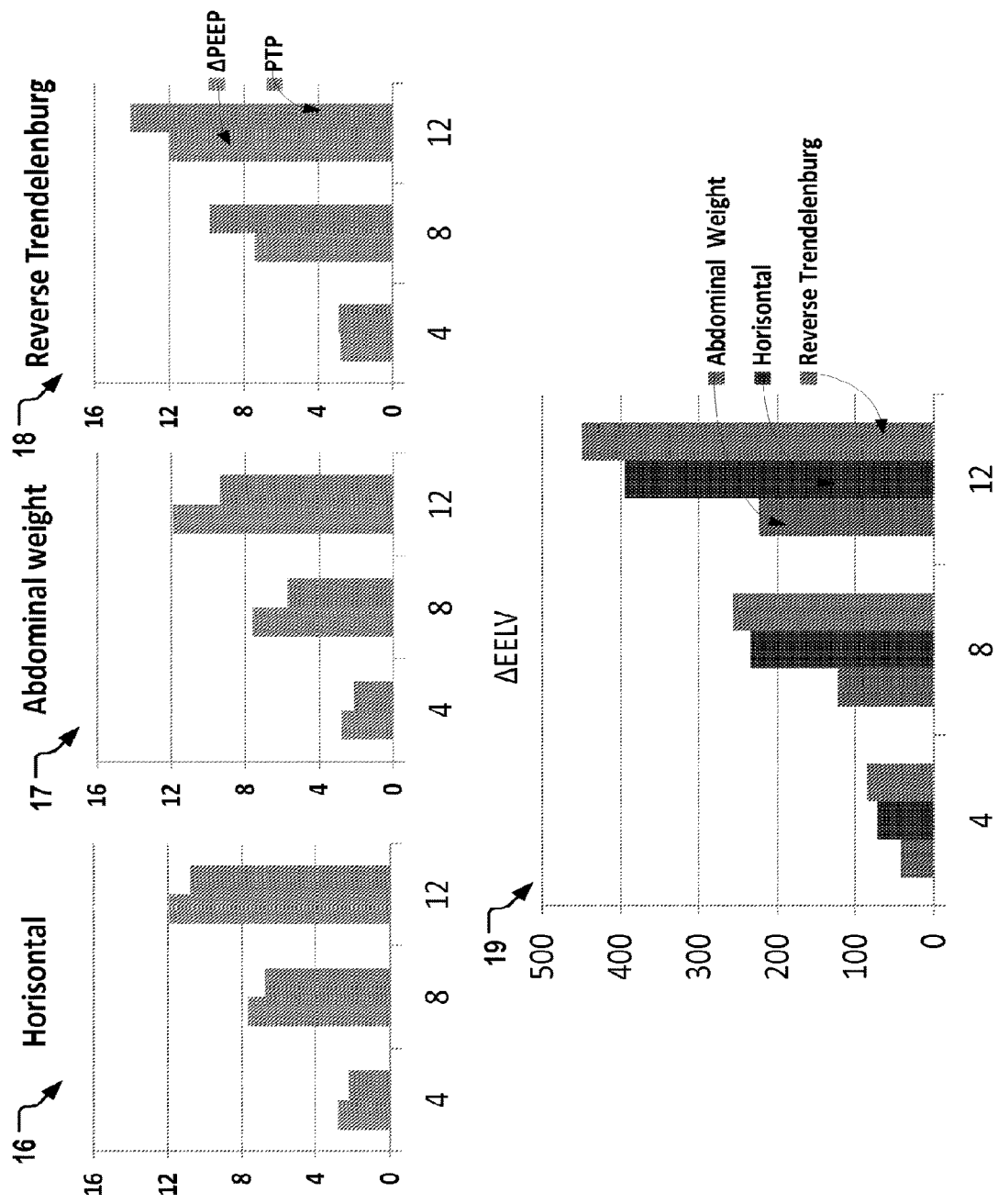
FIG. 14 is a number of graphs 16, 17, 18, 19 showing changes in transpulmonary pressure in different settings.

FIG. 14 is a number of graphs in which it is compared to the change in transpulmonary pressure of a tidal volume of the same size as the ΔEELV following a PEEP change. During abdominal loading the conventional transpulmonary pressure is lower than the ΔPEEP as the inertia of the abdominal cavity fluid and organs prevents a rapid displacement of the diaphragm. In contrast, the conventionally measured transpulmonary pressure is higher than the ΔPEEP during reverse Trendelenburg as the fluid and organs of the abdominal cavity are displaced in caudal direction by gravity.

Using data from previously published studies, we performed a comparison of conventionally determined (using esophageal pressure measurements) lung compliance in lung healthy patients and patients with moderate and severe respiratory failure with determination of ΔEELV/ΔPEEP and found a very good correlation ($r^2=0.96$), see Table 2 below.

TABLE 2

Lung compliance in patients with ALI: Effects of PEEP. Based on data from Pelosi et al. Recruitment and derecruitment during acute respiratory failure: an experimental study. Am J Respir Crit Care Med. 2001 Jul 1; 164(1): 122-30:

|  |  | PEEP step, cmH$_2$O | | |
| --- | --- | --- | --- | --- |
|  |  | 0-5 | 5-10 | 10-15 |
| Normal | ΔEELV, ml | 516 | 515 |  |
|  | ΔEELV/ΔPEEP, ml/cmH$_2$O | 103 | 103 |  |
|  | CL conventional, ml/cmH$_2$O | 108 | 112 |  |
| Moderate | ΔEELV, ml | 404 | 403 | 359 |
|  | ΔEELV/ΔPEEP, ml/cmH$_2$O | 81 | 76 | 72 |
|  | CL conventional, ml/cmH$_2$O | 72 | 76 | 65 |
| ARDS | ΔEELV, ml | 225 | 246 | 280 |
|  | ΔEELV/ΔPEEP, ml/cmH$_2$O | 45 | 49 | 56 |
|  | CL conventional, ml/cmH$_2$O | 42 | 40 | 38 |

A comparison of transpulmonary pressure with data from patients with pulmonary and extrapulmonary ARDS also showed very good correlation, $r^2=0.991$ see Table 3 below.

TABLE 3

Transpulmonary pressure (PTP) by conventional and Lung Barometry based on data from Gattinoni et al "Acute respiratory distress syndrome caused by pulmonary and extrapulmonary disease. Different syndromes?" Am J Respir Crit Care Med. 1998 July; 158(1): 3-11.

|  | Conventional Method | | | Lung Barometry | | |
| --- | --- | --- | --- | --- | --- | --- |
| PEEP | EE PTP | ΔPTP | Total PTP | EE PTP | ΔPTP | Total PTP |
| Pulmonary ARDS | | | | | | |
| 0 | 0 | 14 | 14 | 0 | 16 | 16 |
| 5 | 4 | 14 | 19 | 5 | 17 | 22 |
| 10 | 9 | 15 | 23 | 10 | 19 | 29 |
| 15 | 12 | 18 | 31 | 15 | 20 | 35 |
| Extrapulmonary ARDS | | | | | | |
| 0 | 0 | 10 | 10 | 0 | 13 | 13 |

TABLE 3-continued

Transpulmonary pressure (PTP) by conventional and Lung Barometry based on data from Gattinoni et al "Acute respiratory distress syndrome caused by pulmonary and extrapulmonary disease. Different syndromes?" Am J Respir Crit Care Med. 1998 July; 158(1): 3-11.

|  | Conventional Method | | | Lung Barometry | | |
| --- | --- | --- | --- | --- | --- | --- |
| PEEP | EE PTP | ΔPTP | Total PTP | EE PTP | ΔPTP | Total PTP |
| 5 | 3 | 9 | 13 | 5 | 10 | 15 |
| 10 | 8 | 9 | 16 | 10 | 10 | 20 |
| 15 | 12 | 8 | 20 | 15 | 9 | 24 |

EE = end-expiratory

In summary of the study, following an increase in PEEP there was a successive build-up of a new EELV. This was a process which occurred over several breaths. The results of the studies confirm the feasibility, effect and efficiency of transpulmonary pressure determination. It was seen that a PEEP increase results in a multi-breath successively decreasing build-up of end-expiratory lung volume. The number of breaths needed to reach this volume depends on the relation between chest wall and lung mechanics. Significantly less breaths are needed with higher lung vs chest wall elastance. End-expiratory esophageal pressure did not increase further after the first expiration following a PEEP increase (step) even though end-expiratory pressure continued to increase.

It is concluded that the balance between lung and chest wall elastance has clear influence on PEEP induced inflation of the respiratory system. The increase in end expiratory lung volume was observed to be fairly proportional to the magnitude of the PEEP step divided by lung elastance. In addition PEEP increase results in a less than expected increase in esophageal pressure indicating that the chest wall and abdomen gradually can accommodate changes in lung volume by stress adaptation and by the previously described rib cage end-expiratory spring-out force which counteracts the recoil of the lung over a wide range of PEEP-levels.

These effects are regarded surprisingly and advantageous, encouraging determination of transpulmonary pressure and to separate lung and chest wall mechanics in a clinical setting, only using data available in the ventilator.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

The invention claimed is:

1. A breathing apparatus for non-spontaneous controlled positive pressure ventilation, comprising:
   an inspiratory valve;
   an expiratory valve; and
   a control unit, the control unit configured to:
      determine a target Positive End Expiratory Pressure (PEEP) level based on a transpulmonary pressure ($P_{tp}$) of a patient;
      set the breathing apparatus to ventilate the patient based on the target PEEP level by controlling the inspiratory and expiratory valves; and
      determine the transpulmonary pressure ($P_{tp}$) based on a change in end-expiratory lung volume (ΔEELV) in the patient when ventilated from a first PEEP level to a second PEEP level and based on a difference between the first PEEP level and the second PEEP level (ΔPEEP), wherein the breathing apparatus is configured to ventilate the patient by non-spontaneous controlled positive pressure ventilation.

2. The breathing apparatus of claim 1, wherein the control unit is further configured to:
determine (i) a critical opening pressure corresponding to a pressure indicative of lung air sac collapse and (ii) an overinflation pressure corresponding to a pressure indicative of lung overinflation; and
adjust online the target PEEP level to maintain the target PEEP level between the critical opening pressure and the overinflation pressure, thereby preventing air sac collapse or overinflation of a lung of the patient.

3. The breathing apparatus of claim 1, wherein the control unit is further configured to:
set the breathing apparatus in a first mode of operation for ventilating the patient with a first PEEP level by controlling the inspiratory and expiratory valves;
set the breathing apparatus in a second mode of operation for ventilating the patient with a second PEEP level by controlling the inspiratory and expiratory valves;
determine a change in end-expiratory lung volume (ΔEELV) from a difference of end-expiratory lung volume (EELV) present at said first PEEP level and said second PEEP level; and
determine a change in transpulmonary pressure ($\Delta P_{tp}$) based on the change in end-expiratory lung volume (ΔEELV) and a difference between the first PEEP level and the second PEEP level (ΔPEEP).

4. The breathing apparatus of claim 3, wherein the control unit is further configured to determine ΔEELV based on a change in end-expiratory impedance (ΔZ) following the change in PEEP level.

5. The breathing apparatus of claim 4, wherein the control unit is further configured to determine ΔEELV by converting ΔZ to ΔEELV based on a mean value of ΔZ/ΔEELV at the first and second PEEP levels.

6. The breathing apparatus of claim 3, wherein the control unit is further configured to determine a change in transpulmonary pressure (ΔPtp) in a patient connected to the apparatus based on ΔEELV and a difference between the first and second PEEP levels (ΔPEEP).

7. The breathing apparatus of claim 3, wherein the control unit is further configured to, after the determination of change in the transpulmonary pressure (ΔPtp), set the apparatus in a third mode of operation for ventilating a patient with the first PEEP level by controlling the inspiratory and expiratory valves.

8. The breathing apparatus of claim 1, further comprising one or more flow transducers, wherein the control unit is further configured to determine a change in end-expiratory lung volume (ΔEELV) from spirometric measurements of the one or more flow transducers.

9. An apparatus, comprising:
one or more flow transducers; and
a control unit configured to:
utilize the one or more flow transducers to make one or more spirometric measurements of an inspiratory tidal volume and an expiratory tidal volume;
determine, based on the one or more spirometric measurements, a cumulative difference between the inspiratory and expiratory tidal volumes until the inspiratory and expiratory tidal volumes reach equilibrium;
determine a change in end-expiratory lung volume (ΔEELV) based on the cumulative difference between the inspiratory and expiratory tidal volumes;
determine a transpulmonary pressure ($P_{tp}$) of a patient based on the ΔEELV;
determine a target Positive End Expiratory Pressure (PEEP) level based on the $P_{tp}$; and
ventilate the patient based on the target PEEP level by controlling an inspiratory valve and an expiratory valve.

10. The apparatus of claim 9, wherein:
the one or more spirometric measurements are made in response to a change of Positive End Expiratory Pressure (PEEP) level, the change in PEEP level being from a first PEEP level to a second PEEP level, and
the determination of the cumulative difference between the inspiratory and expiratory tidal volumes occurs until the inspiratory and expiratory tidal volumes reach equilibrium at the second PEEP level.

11. The apparatus of claim 9, wherein the control unit is further configured to:
determine the inspiratory and expiratory tidal volumes reach equilibrium at the first PEEP level;
set the apparatus in a mode of operation for ventilating a patient with the second PEEP level by controlling the inspiratory and expiratory valves; and
determine the cumulative difference between the inspiratory and expiratory tidal volumes until the inspiratory and expiratory tidal volumes reach equilibrium at the second PEEP level.

12. The apparatus of claim 11, wherein the control unit is further configured to determine ΔEELV based on a change in end-expiratory impedance (ΔZ) following the change in PEEP level.

13. The apparatus of claim 12, wherein determining ΔEELV further comprises converting ΔZ to ΔEELV based on a mean value of ΔZ/ΔEELV at the first and second PEEP levels.

14. The apparatus of claim 9, wherein the control unit is further configured to determine a change in transpulmonary pressure (ΔPtp) in a patient connected to the apparatus based on ΔEELV and a difference between the first and second PEEP levels (ΔPEEP).

15. The apparatus of claim 9, wherein the control unit is further configured to:
detect whether the inspiratory and expiratory tidal volumes reach equilibrium; and
determine a change in transpulmonary pressure (ΔPtp) based on a difference between the first PEEP level and the second PEEP level (ΔPEEP) when the equilibrium is established.

16. A method of determining a change in end-expiratory lung volume (ΔEELV), the method comprising:
making one or more spirometric measurements of an inspiratory tidal volume and an expiratory tidal volume;
determining, based on the one or more spirometric measurements, a cumulative difference between the inspiratory and expiratory tidal volumes until the inspiratory and expiratory tidal volumes reach equilibrium;
determining the ΔEELV based on the cumulative difference between the inspiratory and expiratory tidal volumes;

determining a transpulmonary pressure ($P_{tp}$) of a patient based on the ΔEELV;

determining a target Positive End Expiratory Pressure (PEEP) level based the $P_{tp}$; and ventilating the patient with a breathing apparatus based on the target PEEP level by controlling inspiratory and expiratory valves.

17. The method of claim 16, wherein:

the one or more spirometric measurements are made in response to a change of Positive End Expiratory Pressure (PEEP) level, the change in PEEP level being from a first PEEP level to a second PEEP level; and the determination of the cumulative difference between the inspiratory and expiratory tidal volumes occurs until the inspiratory and expiratory tidal volumes reach equilibrium at the second PEEP level.

18. The method of claim 16, further comprising determining ΔEELV based on a change in end-expiratory impedance (ΔZ) following the change in PEEP level.

19. The method of claim 16, wherein determining ΔEELV comprises converting ΔZ to ΔEELV based on a mean value of ΔZ/ΔEELV at the first and second PEEP levels.

20. The method of claim 16, further comprising: determining a change in transpulmonary pressure (ΔPtp) in a patient based on ΔEELV and a difference between the first and second PEEP levels (ΔPEEP).

21. The method of claim 16, further comprising: when the inspiratory and expiratory tidal volumes reach equilibrium, determine a change in transpulmonary pressure (ΔPtp) in a patient based on a difference between the first PEEP level and the second PEEP level (ΔPEEP).

22. The method of claim 16, wherein determining lung compliance (CL) and/or chest wall compliance (Ccw) further comprises at least one of:

repeating one or more PEEP level changes smaller than an initial difference between the first and second PEEP levels;

reducing a tidal volume for detecting a deflection point of a total compliance ($C_{TOT}$); and increasing PEEP from the first PEEP level stepwise until a sum of the stepwise obtained ΔEELV (ΣΔEELV) is substantially equal to a tidal volume at the first PEEP level.

23. A method of adjusting a Positive End Expiratory Pressure (PEEP) level in a breathing apparatus ventilating a patient, the method comprising:

determining, by a control unit, a target Positive End Expiratory Pressure (PEEP) level based on a transpulmonary pressure ($P_{tp}$) of the patient, wherein the transpulmonary pressure ($P_{tp}$) of the patient is based on a change in end-expiratory lung volume (ΔEELV) in the patient when ventilated from a first PEEP level to a second PEEP level and based on a difference between the first PEEP level and the second PEEP level (ΔPEEP);

setting the breathing apparatus to ventilate the patient with the target PEEP level by controlling an inspiratory valve and an expiratory valve of said breathing apparatus; and providing a non-spontaneously controlled positive pressure ventilation to ventilate the patient.

24. A breathing apparatus for ventilation of a patient, comprising:

an inspiratory valve;

an expiratory valve;

wherein the breathing apparatus is configured to ventilate the patient by non-spontaneous controlled positive pressure ventilation and a control unit, the control unit configured to:

determine a target Positive End Expiratory Pressure (PEEP) level based on a transpulmonary pressure ($P_{tp}$) of a patient independently of oesophageal pressure measurements; and set the breathing apparatus to ventilate the patient based on the target PEEP level by controlling the inspiratory and expiratory valves.

25. A method of adjusting a Positive End Expiratory Pressure (PEEP) level in a breathing apparatus ventilating a patient, the method comprising:

providing a non-spontaneously controlled positive pressure ventilation to ventilate the patient; and determining a target Positive End Expiratory Pressure (PEEP) level based on a transpulmonary pressure ($P_{tp}$) of the patient independently of oesophageal pressure measurements; and setting the breathing apparatus to ventilate the patient with the target PEEP level by controlling an inspiratory valve and an expiratory valve of said breathing apparatus.

* * * * *